(12) United States Patent
Takagi

(10) Patent No.: US 11,175,283 B2
(45) Date of Patent: Nov. 16, 2021

(54) METHOD FOR PROCESSING BLOOD SAMPLE

(71) Applicant: ARKRAY, Inc., Kyoto (JP)

(72) Inventor: Hidenori Takagi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 1360 days.

(21) Appl. No.: 14/495,127

(22) Filed: Sep. 24, 2014

(65) Prior Publication Data

US 2015/0087016 A1    Mar. 26, 2015

(30) Foreign Application Priority Data

Sep. 25, 2013 (JP) .............................. JP2013-198311
Sep. 11, 2014 (JP) .............................. JP2014-185274

(51) Int. Cl.
| | |
|---|---|
| *G01N 33/49* | (2006.01) |
| *G01N 33/50* | (2006.01) |
| *B01D 35/30* | (2006.01) |
| *B01D 29/03* | (2006.01) |

(52) U.S. Cl.
CPC ......... *G01N 33/5094* (2013.01); *B01D 29/03* (2013.01); *B01D 35/30* (2013.01); *G01N 33/491* (2013.01)

(58) Field of Classification Search
None
See application file for complete search history.

(56) References Cited

U.S. PATENT DOCUMENTS

| | | | |
|---|---|---|---|
| 2007/0025883 A1* | 2/2007 | Tai | ......................... B01D 61/14 422/400 |
| 2010/0248207 A1 | 9/2010 | Raz et al. | |
| 2011/0294206 A1 | 12/2011 | Tai et al. | |
| 2012/0178097 A1* | 7/2012 | Tai | ....................... B01D 63/087 435/7.1 |
| 2012/0276555 A1 | 11/2012 | Kuhn et al. | |

FOREIGN PATENT DOCUMENTS

| | | |
|---|---|---|
| CN | 102782498 A | 11/2012 |
| JP | 2008-538509 A | 10/2008 |
| JP | 2010-530234 A | 9/2010 |
| JP | 2011-163830 A | 8/2011 |
| JP | 5086241 B2 | 11/2012 |
| JP | 2013-017429 A | 1/2013 |
| WO | 2006/116327 A1 | 11/2006 |
| WO | 2007/089911 A2 | 8/2007 |

OTHER PUBLICATIONS

Office Action issued in corresponding Chinese Patent Application No. 201410498324.2 dated Dec. 28, 2016.
(Continued)

*Primary Examiner* — Krishnan S Menon
*Assistant Examiner* — Brad Gordon
(74) *Attorney, Agent, or Firm* — Morgan, Lewis & Bockius LLP

(57) ABSTRACT

A method for processing a blood sample is provided that can improve the recovery rate of deformable rare cells that would easily pass through a filter and small rare cells while reducing the filtration area of the filter, and that can recover the rare cells alive.

20 Claims, 8 Drawing Sheets

Photographs were taken with a laser microscope (objective lens magnification: 50X).

(56) References Cited

OTHER PUBLICATIONS

Dotan et al., "Circulating Tumor Cells: Evolving Evidence and Future Challenges," The Oncologist: Cancer Diagnostics and Molecular Pathology, 14: 1070-1082 (2009).
Martin et al., "Immunomagnetic enrichment of disseminated epithelial tumor cells from peripheral blood by MACS," Experimental Hematology, 26: 252-264 (1998).
Yang et al., "Optimization of an Enrichment Process for Circulating Tumor Cells From the Blood of Head and Neck Cancer Patients Through Depletion of Normal Cells," Biotechnology and Bioengineering, 102: 521-534 (2009).
Gertler et al., "Detection of Circulating Tumor Cells in Blood Using an Optimized Density Gradient Centrifugation," Cancer Research, 162: 149-155 (2003).
Baker et al., "Molecular Detection of Breast Cancer Cells in the Peripheral Blood of Advanced-Stage Breast Cancer Patients Using Multimarker Real-Time Reverse Transcription—Polymerase Chain Reaction and a Novel Porous Barrier Density Gradient Centrifugation Technology," Clinical Cancer Research, 9: 4865-4871 (2003).
Rostagno et al., "Detection of Rare Circulating Breast Cancer Cells by Filtration Cytometry and Identification by DNA Content: Sensitivity in an Experimental Model," Anticancer Research, 17: 2481-2486 (1997).
Vona et al., "Isolation by Size of Epithelial Tumor Cells: A New Method for the Immunomorphological and Molecular Characterization of Circulating Tumor Cells," American Journal of Pathology, 156: 57-63 (2000).
Farace et al., "A direct comparison of CellSearch and ISET for circulating tumour-cell detection in patients with metastatic carcinomas," British Journal of Cancer, 105: 847-853 (2011).
Zheng et al., "Membrane microfilter device for selective capture, electrolysis and genomic analysis of human circulating turmor cells," Journal of Chromatography A, 1162: 154-161 (2007).
Lin et al., "Portable Filter-Based Microdevice for Detection and Characterization of Circulating Tumor Cells," Clinical Cancer Research, 16: 5011-5018 (2010).
Hosokawa et al., "Size-Selective Microcavity Array for Rapid and Efficient Detection of Circulating Tumor Cells," Analytical Chemistry, 82: 6629-6635 (2010).
Zheng et al., "3D microfilter device for viable circulating tumor cell (CTC) enrichment from blood," Biomed Microdevices, 13: 203-213 (2011).
Coumans et al., "Filter Characteristics Influencing Circulating Tumor Cell Enrichment from Whole Blood," PLOS One, 8: e61770, 1-12 (2013).
Park et al., "Morphological Differences between Circulating Tumor Cells from Prostate Cancer Patients and Cultured Prostate Cancer Cells," PLOS One, 9: e85264, 1-7 (2014).
Guck et al., "Optical Deformability as an Inherent Cell Marker for Testing Malignant Transformation and Metastatic Competence," Biophysical Journal, 88: 3689-3698 (2005).
Xu et al., "Cell Stiffness Is a Biomarker of the Metastatic Potential of Ovarian Cancer Cells," PLOS One, 7: e46609 1-12 (2012).
Extended European Search Report issued in related European Patent Application No. 14186437.1 dated Jan. 22, 2015.
Office Action issued in corresponding Chinese Patent Application No. 201410498324.2 dated Mar. 28, 2018 (see partial English translation).
Office Action issued in corresponding Japanese Patent Application No. 2014-185274 dated Apr. 24, 2018.

* cited by examiner

Photographs were taken with a laser microscope (objective lens magnification: 50X).

METHOD FOR PROCESSING BLOOD SAMPLE

BACKGROUND OF THE INVENTION

1. Field of the Invention

The present disclosure relates to a method for processing a blood sample, a method for separating rare cells in a blood sample, a method for enumerating or analyzing circulating tumor cells in blood, a filter used in these methods, and a device for capturing rare cells.

2. Description of Related Art

The blood cell components are mainly red blood cells, white blood cells, and platelets. In some cases, cells other than these blood cells may be found in blood. Circulating tumor cells (CTCs) are one example of such cells. Metastasis of cancer is attributed to the transfer and growth of cancer cells to a distant site in the body through the blood or lymphatic vessels. It has been reported that there is a relationship between the number of CTCs in blood and the risk and prognosis of metastasis of cancer. The enumeration of CTCs in blood and the measurement of the nucleic acids of CTCs are known to be used as indicators of diagnosis, prognosis, and the prediction or evaluation of a therapeutic effect of cancer (particularly metastatic cancer such as breast cancer). Various techniques for separating and concentrating CTCs have been proposed and studied (see Non-Patent Documents 1 to 16 and Patent Documents 1 to 4).

PRIOR ART DOCUMENTS

Patent Documents

Patent Document 1: Japanese Patent No. 5086241
Patent Document 2: JP 2011-163830 A
Patent Document 3: JP 2013-17429 A
Patent Document 4: JP 2010-530234 A Non-Patent Documents Non-Patent Document 1: EFRAT DOTAN, STEVEN J. COHEN, KATHERINE R. ALPAUGH, NEAL J. MEROPOL, Evolving Evidence and Future Challenges, The oncologist 2009; 14; 1070-1082

Non-Patent Document 2: Martin V M, Siewert C, Scharl A, Harms T, Heinze R, Ohl S, Radbruch A, Miltenyi S, Schmitz J, Immunomagnetic enrichment of disseminated epithelial tumor cells from peripheral blood by MACS. Exp Hematol. 1998 March; 26(3): 252-64

Non-Patent Document 3: L. Yang, J. C. Lang, P. Balasubramanian, K. R. Jatana, D. Schuller, et al., Optimization of an Enrichment Process for Circulating Tumor Cells From the Blood of Head and Neck Cancer Patients Through Depletion of Normal Cells, Biotechnol Bioeng; 102(2): 521-534 (2009)

Non-Patent Document 4: Ralf Gertler, Robert Rosenberg, Katrin Fuehrer, Michael Dahm, Hjalmar Nekarda, Joerg Ruediger Siewert, Detection of Circulating Tumor Cells in Blood Using an Optimized Density Gradient Centrifugation Recent Results in Cancer Research Volume 162, 2003, pp 149-155

Non-Patent Document 5: M. K. Baker, K. Mikhitarian, W. Osta, et al., Molecular detection of breast cancer cells in the peripheral blood of advanced-stage breast cancer patients using multimarker real-time reverse transcription-polymerase chain reaction and a novel porous barrier density gradient centrifugation technology, Clin Cancer Res; 9: 4865-4871 (2003)

Non-Patent Document 6: Rostagno P, Moll J L, Bisconte J C, Caldani C, Detection of rare circulating breast cancer cells by filtration cytometry and identification by DNA content: sensitivity in an experimental model, Anticancer Res. 1997, 17, 2481-2485

Non-Patent Document 7: G. Vona, A. Sabile, M. Louha, et al., Isolation by size of epithelial tumor cells: a new method for the immunomorphological and molecular characterization of circulating tumor cells, Am J Pathol; 156: 57-63 (2000)

Non-Patent Document 8: F. Farace, C. Massard, N. Vimond, F. Drusch, et al., A direct comparison of CellSearch and ISET for circulating tumour-cell detection in patients with metastatic carcinomas, Br J Cancer; 105(6): 847-853 (2011)

Non-Patent Document 9: S. Zheng, H. Lin, J. Q. Liu, et al., Membrane microfilter device for selective capture, electrolysis and genomic analysis of human circulating tumor cells, J Chromatogr A; 1162: 154-61 (2007)

Non-Patent Document 10: H. K. Lin, S. Zheng, A. J. Williams, et al., Portable filter-based microdevice for detection and characterization of circulating tumor cells, Clin Cancer Res; 16(20): 5011-5018 (2010)

Non-Patent Document 11: Hosokawa M, Hayata T, Fukuda Y, Arakaki Ai, et al., Anal. Chem., 2010, 82 (15), pp 6629-6635, Size-Selective Microcavity Array for Rapid and Efficient Detection of Circulating Tumor Cells Non-Patent Document 12: S. Zheng, H. K. Lin, B. Lu., 3D microfilter device for viable circulating tumor cell (CTC) enrichment from blood, Biomed Microdevices; 13: 203-213 (2011)

Non-Patent Document 13: Frank A. W. Coumans, Guus van Dalum, Markus Beck, Leon W. M. M. Terstappen* Filter Characteristics Influencing Circulating Tumor Cell Enrichment from Whole Blood, April 2013, Volume 8, Issue 4, e61770

Non-Patent Document 14: Sunyoung Park, Richard R. Ang, Simon P. Duffy, Jenny Bazov, Kim N. Chi, Peter C. Black, Hongshen Ma, Morphological differences between circulating tumor cells from prostate cancer patients and cultured prostate cancer cells, January 2014, Volume 9, Issue 1, e85264

Non-Patent Document 15: Jochen Guck, Stefan Schinkinger, Bryan Lincoln, Falk Wottawah, Susanne Ebert, Maren Romeyke, Dominik Lenz, Harold M. Erickson, Revathi Ananthakrishnan, *Daniel Mitchell, Josef Kas, Optical Deformability as an Inherent Cell Marker for Testing Malignant Transformation and Metastatic Competence, Biophysical Journal, Volume 88, May 2005, 3689-3698

Non-Patent Document 16: Wenwei Xu, Roman Mezencev, Byungkyu Kim, Lijuan Wang, John McDonald, Todd Sulchek, October 2012, Volume 7, Issue 10, e46609, Cell Stiffness Is a Biomarker of the Metastatic Potential of Ovarian Cancer Cells

SUMMARY OF THE INVENTION

Conventionally, with respect to blood and CTCs, the predominance of red blood cells and white blood cells has made it difficult to detect or obtain cells that are found in blood at much lower levels. For example, the CELL-SEARCH system, which is approved by the Food and Drug Administration (FDA) at present, uses an EpCAM antibody as a surface marker of cancer cells. However, the CELL- SEARCH system detects tumor cells that express few or no EpCAM or cytokeratin (CK). Therefore, the ability of the CELLSEARCH system to capture cancer cells is limited, since it utilizes affinity and relies on the amount of antigen expressed. The CELLSEARCH system employs fixation and antibodies for separation and concentration of CTCs. However, due to the reliance on the amount of surface antigen expressed by CTCs, some cells cannot be captured by the CELLSEARCH system. Thus, even if CTCs are actually traveling in blood, the CELLSEARCH system may not capture many of them and results in low sensitivity. There has been a demand for a method that can separate CTCs without relying on antibodies.

Non-Patent Documents 6 to 8 disclose a method for separating CTCs in view of the fact that (i) the cancer cells are generally larger than the blood cells and (ii) the inherent flexibility and deformability of the blood cells allow the white blood cells to pass through holes smaller than themselves. However, the method uses a filter with non-uniform holes, and some of them are fused together into large holes. Thus, the cancer cells can go through these holes, which leads to a low capture rate.

On the other hand, in contrast to a track-etched membrane filter (polycarbonate filter; PC filter), a new filter for capturing CTCs has been proposed that is made of a plastic or metal material and includes uniform holes, thereby improving the capture rate. This filter has been proved to achieve a higher capture rate than the CELLSEARCH system. As a technique for separating and detecting CTCs in blood, Patent Document 1 discloses a parylene membrane filter including uniform holes for the separation of CTCs. Patent Document 2 discloses a size-selective micro cavity array (metal filter) having a filtration area of 99 $\mu m^2$ (hole diameter: $\phi$ 10 $\mu m$, hole number: 10000). The size-selective micro cavity array is used to separate CTCs from 1 ml of blood, and the hole diameter can be controlled to $\phi$ 8 $\mu m$ so as to capture small cancer cells that would pass through $\phi$ 10 $\mu m$ holes. Incidentally, plastic and metal filters have a high capture rate, although their surface characteristics are different. This is because both filters are based on the filtration principle that cells larger than the holes are retained on the filter. In other words, the hole size serves as the most important factor that will affect the capture efficiency of cells by filtration. Thus, other materials can also be expected to provide the same effect.

The presence of small CTCs (average size: 7.97 $\mu m$) has recently been reported (see Non-Patent Documents 13 to 14). A filter that includes at least 100000 holes (hole diameter: $\phi$ 5 $\mu m$) in order for 1 ml of blood to pass through the holes has been proposed. This filter has an open area ratio of 10% or less and is expected to capture small CTCs.

Moreover, highly deformable cancer cells have been found (see Non-Patent Documents 14 to 15). These cells are very likely to be malignant cancer cells that may cause metastasis. If the highly deformable cancer cells are captured, the gene analysis of CTCs can proceed and the treatment of cancer can be improved.

CTCs are extremely promising for the medical development. However, as described above, there are only a few CTCs in 10 ml of blood. Assuming that two CTCs are present in 10 ml of blood, when 1 ml of blood is processed, the probability of one or more CTCs being detected is about 20% according to the Poisson distribution. Therefore, even if all the CTCs can be captured, the detection rate is 20% at most. On the contrary, when blood can be processed in large volume (e.g., 8 ml), the probability of one or more CTCs being detected reaches about 90%. Thus, a filter is required to be able to process a large amount of blood appropriately.

If the filters disclosed in the above documents include holes with a diameter larger than 10 $\mu m$, they cannot capture small cells that would pass through holes with a diameter of about 10 $\mu m$ because the cell size is smaller than the hole diameter. For example, to capture cells having a predetermined size, a filter may generally be designed to have a hole diameter smaller than the predetermined size. Actually, however, when the hole diameter is simply reduced, not only the target cells but also the blood cells are likely to be captured. Therefore, the filter will be easily clogged as the hole diameter becomes smaller. Consequently, the flow of a fluid is interrupted, and the filtration time is increased. To deal with this issue, the fluid may be quickly processed by increasing pressure applied to the filter during filtration (i.e., filtration pressure). However, such an increase in pressure will force the cells through the filter or will probably damage the cells as they come into contact with the holes.

For example, Patent Document 3 discloses a method for capturing small cancer cells. In this method, blood is hemolyzed to reduce the blood cell count, and subsequently is processed using a filter that has a diameter of 25 mm (area: 490 $mm^2$) and includes small holes with a minor axis diameter of 5 $\mu m$ and a major axis diameter of 5 $\mu m$. Patent Document 3 also discloses the example in which a total of 1 ml of diluted blood is filtered through a paper filter (hole diameter: 0.4 $\mu m$) so that white blood cells are collected. However, it seems unlikely that the target cells (the white blood cells in the example) can be appropriately collected by filtering more than 1 ml of blood in total. The amount of blood processed in the example of Patent Document 3 is not enough to ensure the capture efficiency when rare cells such as CTCs are to be detected, since the rare cells may be found in blood at considerably low frequency (e.g., only a few cells are present in 10 ml of blood). Therefore, a large amount of blood needs to flow through the filter. Thus, the use of the method taught by Patent Document 3 would require an enlarged filter area, causing an increase in the cost of reagents used for the cell detection and also an increase in the amounts of cleaning fluid and waste fluid. Moreover, the operation process would be complicated.

As described above, when the hole diameter is simply reduced, a large amount of blood cannot be processed. In addition, to avoid clogging of the filter, it is necessary to increase the filtration area (i.e., the area of a portion of the filter through which a fluid can be filtered) and the number of the holes (hole number) of the filter. This in turn increases the bulk of a device and the labeling reagents to be used (which are generally expensive), so that the cost is increased. Moreover, the strength of the filter is reduced by an increase in hole density, and the durability of a membrane also is reduced by a decrease in pitch between the holes. In this case, if the thickness of the membrane is increased to improve the durability, the pressure required for blood to flow has to be increased. Thus, a heavy load may be imposed on the cells, and further clogging is likely to occur. Moreover, many cells other than the target cells remain on the filter and can interfere with the analysis.

On the other hand, in order to capture deformable cells, a pressure difference ($\Delta P_2$) between the upper surface and the lower surface of a filter may be reduced, making it difficult for the cells to pass through the holes in the filter. According to the Hagen-Poiseuille law, a pressure difference ($\Delta P$) between the upper portion and the lower portion of one true circular hole of a filter is given by $\Delta P = 8\eta L/\pi d^4 \times Q$, where Q represents the flow rate, $\eta$ represents the viscosity, L represents the thickness, and d represents the hole radius. If the hole diameter of the filter is changed from φ 8 μm to φ 9 μm or φ 10 μm, while the flow rate is unchanged, the pressure difference (ΔP) is increased by about 0.6 times or about 0.4 times, and thus the number of cells captured is expected to be increased. However, if the hole diameter is more than 10 μm, the possibility of capturing small cancer cells is reduced, even though deformable cells can be captured. The capture rate may be improved by reducing the amount of fluid flowing per unit time (flow rate) so as to lower the load on the holes in the filter. When such a measure is actually taken, however, the capture rate of cells with high deformability may be reduced.

Patent Document 4 discloses a technology for separating cancer cells and white blood cells by the difference in viscoelasticity. In other words, the invention of Patent Document 4 uses the difference in the properties between the white blood cells and the cancer cells. Specifically, the white blood cells are deformable and can pass through holes smaller than themselves, while the cancer cells are less deformable compared to the blood cells and cannot easily pass through holes smaller than themselves. According to Patent Document 4, the separation is facilitated when the target cells are stiffer than the blood cells. In fact, however, there are also cancer cells that have a diameter as large as 10 μm or more, but are highly deformable to the extent that they can easily pass through circular holes in a filter having a diameter of 5 μm to 6.5 μm. To prevent these cancer cells from passing through the filter, the hole diameter may be reduced, as taught by Patent Document 3. However, the method of Patent Document 3 has the above problems. More interestingly, the experiment conducted by the present inventor showed that, under the same conditions where a high capture rate was achieved by filtering a small amount of blood (1 ml), the capture rate of deformable cells was reduced with the amount of the blood sample processed.

In such a case, the capture rate may be improved by a method in which a fixing agent such as paraformaldehyde is added to blood beforehand so that the cells are fixed for separation (see, e.g., Non-Patent Documents 7 to 8, 10). However, this method requires additional measures to suppress clogging of the filter, e.g., by diluting blood to reduce the particle density and increasing the filtration area. Thus, the method becomes more complicated. Moreover, as a result of the fixation, white blood cells also are not likely to pass through the filter. Therefore, the hole size of the filter should be increased, which allows small cancer cells to go through the filter when deformable cancer cells are being captured. In the above fixation method, high pressure needs to be applied to the filter in order to prevent clogging during the filtration of blood. This may cause the target cells to pass through the filter or to be broken. Thus, when the fixation method is used, the hole diameter cannot be simply reduced, and various problems arise, including a reduction in the amount of blood processed per hole or per filtration area, an increase in pressure, an increase in the amount of waste fluid, and the use of toxic substances. Moreover, the fixation method cannot capture and analyze cells alive.

As described above, it is difficult for the conventional method to process a large amount of blood without the fixation while reducing the filtration size or the number of filters, and also to capture viable cancer cells that would pass through holes with a diameter of 10 μm or that would be deformed to pass through circular holes with a diameter of φ 5 μm to φ 6.5 μm.

In one or more embodiments, the present disclosure provides a simple and rapid method for processing a blood sample. This method can improve the capture rate of small rare cells and deformable rare cells that may be present in the blood sample by using a filter in which the shape, area, and number of the holes are set to appropriate values, or by determining a blood volume per hole from the shape, area, and number of the holes in the filter. In this case, the small rare cells can pass through holes with a diameter of 10 μm because the cell size is smaller than the hole diameter, and the deformable rare cells can pass through true circular holes with a diameter of φ 5 μm to φ 6.5 μm when the amount of the blood sample to be processed per hole is 14 nl or more, and whole blood is transferred at 5 nl/min to 20 nl/min per hole. Moreover, this method can capture the above rare cells alive while reducing the area of a portion of the filter that is to be used for the filtration of the blood sample (i.e., the filtration area of the filter).

Here, an appropriate range of the number of the holes in the filter can be determined by the following formula 1.

Hole number (holes)=Total volume of blood sample to be processed (nl)/170 to Total volume of blood sample to be processed (nl)/10  Formula 1:

On the other hand, an appropriate range of the total area of the holes in the filter can be determined by the following formula 2.

Total hole area (μm$^2$)=Total volume of blood sample to be processed (nl)/3.4 (nl/μm$^2$) to Total volume of blood sample to be processed (nl)/0.2 (nl/μm$^2$)  Formula 2:

In one or more embodiments, the present disclosure provides a method for processing a blood sample that can improve the capture rate of rare cells when the rare cells are present in the blood sample.

In one or more embodiments, the present disclosure relates to a method for separating or detecting rare cells in a blood sample using a filter including holes with a hole density of at least 200 holes/mm$^2$ to 40000 holes/mm$^2$, wherein the holes are in the form of an ellipse with a minor axis diameter of 3.0 μm to 15 μm and a major axis diameter of 1.1 times to 3 times as long as the minor axis diameter, or the holes have a shape that contains the ellipse and is in contact with the ellipse on at least two points including both ends of the major axis of the ellipse. The method includes:

(1) using a filter in which the number of the holes is given by Formula 1: "Hole number (holes)=Total volume of blood sample to be processed (nl)/170 to Total volume of blood sample to be processed (nl)/10" or the total area of the holes is given by Formula 2: "Total hole area (μm$^2$)=Total volume of blood sample to be processed (nl)/3.4 (nl/μm$^2$) to Total volume of blood sample to be processed (nl)/0.2 (nl/μm$^2$)"; or (2) separating or detecting rare cells by filtering the blood sample so that a filter capacity per hole of the filter is 10 nl/hole to 170 nl/hole expressed in terms of blood.

In another one or more embodiments, the present disclosure relates to the method for separating or detecting rare cells in a blood sample, wherein the rare cells are selected from the group consisting of cancer cells, circulating tumor cells, vascular endothelial cells, vascular endothelial precursor cells, cancer stem cells, epithelial cells, hematopoietic stem cells, mesenchymal stem cells, embryonal cells, and a combination thereof.

In another one or more embodiments, the present disclosure relates to the method for separating or detecting rare cells in a blood sample, further including labeling the rare cells by a labeling method associated with a detection method selected from the group consisting of a detection method using a radioactive substance, a detection method using a luminous phenomenon, a detection method using a dye, a detection method using magnetic properties, an electrical detection method, an optical detection method, and a combination thereof.

In another one or more embodiments, the present disclosure relates to a method for analyzing rare cells in a blood sample. This method includes separating or detecting rare cells by the above method for separating or detecting rare cells in a blood sample, and then analyzing the rare cells by a method including kinetic observation or activity measurement of the rare cells.

In another one or more embodiments, the present disclosure relates to a filter including holes with a hole density of at least 200 holes/mm$^2$ to 40000 holes/mm$^2$, wherein the holes are in the form of an ellipse with a minor axis diameter of 3.0 μm to 15 μm and a major axis diameter of 1.1 times to 3 times as long as the minor axis diameter, or the holes have a shape that is in contact with the ellipse on at least two points including both ends of the major axis of the ellipse.

In another one or more embodiments, the present disclosure relates to a device for capturing rare cells that captures rare cells in a sample. This device includes an inlet, an outlet, and a flow path connecting the inlet and the outlet, wherein a separation portion that includes the above filter and a filter holder is provided in a position corresponding to a part of the flow path.

According to the present disclosure, in one or more embodiments, not only deformable cancer cells that would easily pass through the filter, but also small cancer cells can be captured alive while reducing the filtration area. Moreover, according to the present disclosure, in one or more embodiments, the capture rate of rare cells can be improved when the rare cells are present in the blood sample.

DETAILED DESCRIPTION OF THE INVENTION

Figure 1:
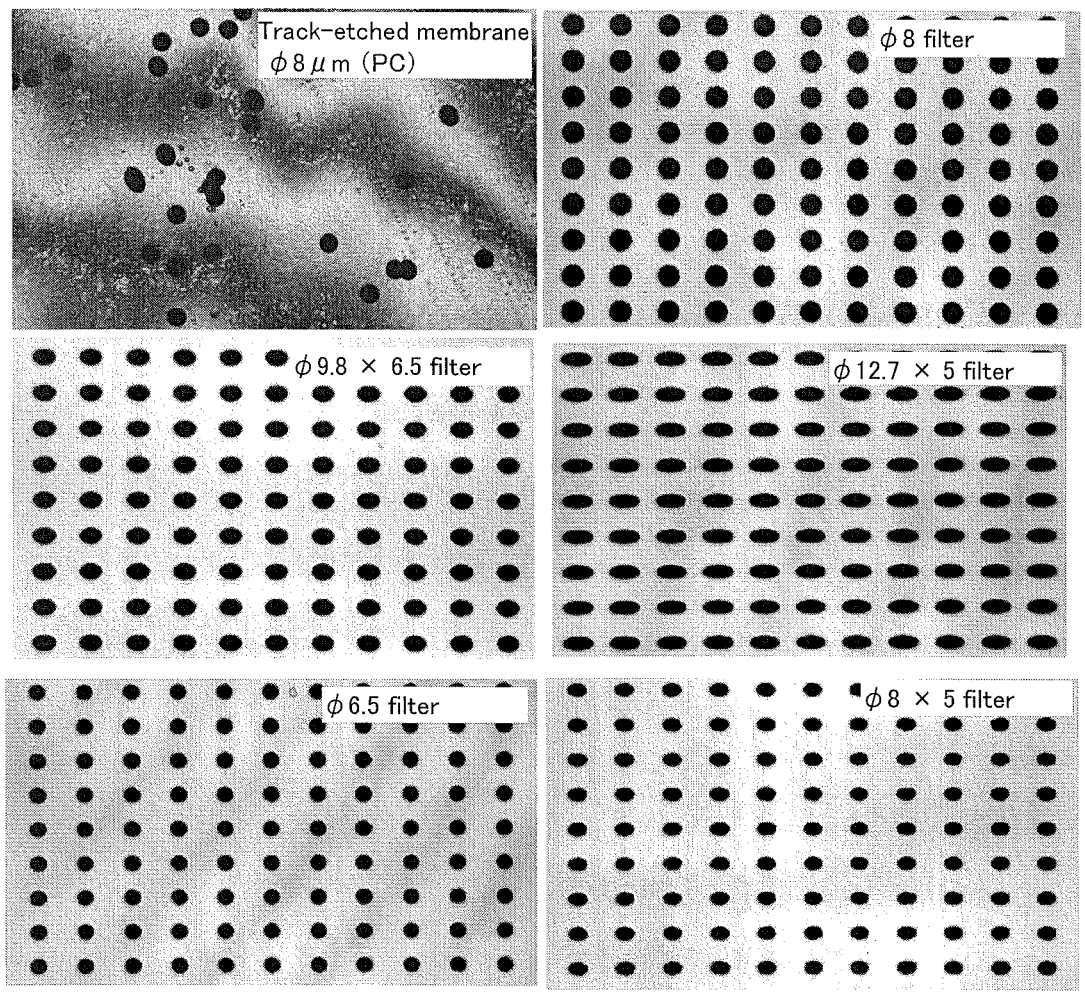
FIG. 1 shows the photographs of filters.

Analysis of rare cells such as circulating tumor cells (CTCs) in blood is expected to continue actively in the future, and there is a growing demand for a simple efficient method. In general, tens of billions of red blood cells and tens of millions of white blood cells are contained in 10 ml of blood, but the number of CTCs only ranges from about zero to several thousands. Therefore, if CTCs are directly analyzed, they will pose many technical problems. Thus, e.g., concentration and separation of CTCs are necessary. It is expected that technology will be developed to concentrate and separate CTCs from blood more efficiently and/or simply.

In one or more embodiments, the present disclosure is based on the findings that rare cells (including relatively small cells and deformable cells) that may be present in a blood sample can be captured alive when the blood sample is filtered by: (i) adjusting the shape and size of the holes in the filter and determining the number of the holes in the filter by the formula: "Hole number (holes)=Total volume of blood sample to be processed (nl)/170 to Total volume of blood sample to be processed (nl)/10" or the formula: "Total hole area (μm$^2$)=Total volume of blood sample to be processed (nl)/3.4 (nl/μm$^2$) to Total volume of blood sample to be processed (nl)/0.2 (nl/μm$^2$)"; or (ii) adjusting the volume of the blood sample passing through the holes in the filter by the formula: "Total volume of blood sample to be processed (nl)=Total hole area (μm$^2$)×0.2 (nl/μm$^2$) to Total hole area (μm$^2$)×3.4 (nl/μm$^2$)".

In one aspect, the present disclosure relates to a method for processing a blood sample that includes filtering the blood sample (also referred to as a "processing method of the present disclosure" in the following).

[Blood Sample]

In the present disclosure, the "blood sample" means a sample that contains blood components and can be applied to the processing method of the present disclosure. Examples of the blood sample include blood, a blood-derived material containing red blood cell components, a body fluid or urine mixed with blood or a blood-derived material, and a sample prepared from these specimens. In the present disclosure, the volume of the blood sample passing through a hole of the filter is set on the basis of blood taken from the human body, i.e., blood containing 1000 to 20000 white blood cells per 1 μl. Therefore, when the blood sample is diluted, the diluted blood sample can be converted into the volume of the blood sample before dilution based on the white blood cell count. For example, when a 10-times diluted blood sample is processed in a volume of "X" μl/hole, it is equivalent to processing the diluted blood sample in a volume of "X/10" μl/hole. The blood can be taken from the living organisms such as humans or animals (e.g., mammals) other than humans. The blood-derived material containing the red blood cell components can be materials that are separated or prepared from blood and contain the red blood cell components, or dilutions/concentrates of these materials Examples of the blood-derived material include the following: a blood cell fraction from which plasma has been removed; a blood cell concentrate; freeze-dried blood or freeze-dried blood cells; a sample obtained by hemolyzing whole blood to remove the red blood cell components or a hemolytic sample; centrifuged blood; sedimented blood; washed blood cells; and a specific fraction. Among them, in one or more non-limiting embodiments, the blood sample is preferably blood or blood-derived blood cells containing blood cell components so as to perform simple and rapid processing of the blood sample and to reduce damage to the rare cells in blood.

[Rare Cell]

In the present disclosure, the "rare cells" that may be present in blood or the blood sample mean cells other than the cell components (red blood cells, white blood cells, and platelets) that may be contained in blood of humans or animals other than humans. The rare cells include tumor cells and/or cancer cells. In general, tumor cells or cancer cells circulating in blood are called CTCs. The number of the rare cells in blood depends on the sample, and can be several to several tens and at most several hundreds to several thousands in 10 ml of blood. In one or more embodiments, the "rare cells" are selected from the group consisting of cancer cells, circulating tumor cells, vascular endothelial cells, vascular endothelial precursor cells, cancer stem cells, epithelial cells, hematopoietic stem cells, mesenchymal stem cells, embryonal cells, and a combination of these cells.

The rare cells and/or CTCs in the blood sample may include large cells, small cells, and deformable cells. The large cells can be captured by a filter with a hole diameter of about ϕ 10 μm. The small cells can pass through holes having the above hole size (i.e., a diameter of about ϕ 10 μm). The deformable cells can be deformed to pass through holes with a diameter of ϕ 5 μm to ϕ 6.5 μm when whole blood is transferred at 5 nl/min to 20 nl/min per hole. In one or more embodiments, the present invention relates to a processing method that uses a predetermined filter to separate and/or capture either or both of large deformable rare cells and small rare cells that may be present in the blood sample.

[Filter Capacity]

In the filtration in the processing method of the present disclosure, the number of the holes in a filter or the filter capacity (i.e., the amount of the blood sample passing through the filter, which is referred to as "the total volume of the blood sample to be processed") can be defined by "Hole number (holes)=Total volume of blood sample to be processed (nl)/170 to Total volume of blood sample to be processed (nl)/10" or "Total hole area (μm$^2$)=Total volume of blood sample to be processed (nl)/3.4 (nl/μm$^2$) to Total volume of blood sample to be processed (nl)/0.2 (nl/μm$^2$)". In one or more embodiments, the filter capacity per hole of the filter is 0.005 μl/hole or more, 0.01 μl/hole or more, 0.014 μl/hole or more, 0.015 μl/hole or more, or 0.02 μl/hole or more in terms of maintaining the capture rate of rare cells. In one or more embodiments, the filter capacity per hole of the filter is 1 μl/hole or less, 0.2 μl/hole or less, 0.170 μl/hole or less, 0.163 μl/hole or less, 0.108 μl/hole or less, 0.054 μl/hole or less, 0.028 μl/hole or less, or 0.014 μl/hole or less in terms of processing a large amount of sample at a time, reducing the filtration area of the filter, and capturing deformable cells and small cells without clogging of the filter. In this case, the filter includes many holes, and the amount of the blood sample per hole of the filter means an average value obtained by dividing the amount of the blood sample to be processed through the filter by the number of the holes in the filter. The present inventor found that the deformable cells could be captured by adjusting the filter capacity.

In the filtration in the processing method of the present disclosure, the filter capacity can be defined by "Total volume of blood sample to be processed (nl)=Hole number (holes)×10 to Hole number (holes)×170" or "Total volume of blood sample to be processed (nl)=Total hole area (μm$^2$)× 0.2 (nl/μm$^2$) to Total hole area (μm$^2$)×3.4 (nl/μm$^2$)". In one or more embodiments, the filter capacity is 0.07 ml or more, 0.25 ml or more, 0.5 ml or more, 1 ml or more, more than 1 ml, 2 ml or more, 3 ml or more, or 4 ml or more with respect to a filtration area of 5 mm$^2$ to 10000 mm$^2$. In one or more embodiments, the filter capacity is 6 L or less, 4 L or less, 2 L or less, 400 ml or less, 200 ml or less, 100 ml or less, 80 ml or less, 50 ml or less, 30 ml or less, 25 ml or less, 12 ml or less, 11 ml or less, 10 ml or less, 9 ml or less, or 8 ml or less with respect to a filtration area of 5 mm$^2$ to 10000 mm$^2$ in terms of maintaining the capture rate of rare cells. Alternatively, in one or more embodiments, the filter capacity is in the range of more than 0.2 ml to 130 ml, in the range of 0.8 ml to 90 ml, in the range of 0.8 ml to 60 ml, in the range of 2 ml to 50 ml, or in the range of 2 ml to 40 ml with respect to a filtration area of 15 mm$^2$ to 200 mm$^2$ in terms of processing a large amount of sample at a time, capturing deformable cells, and maintaining the capture rate of rare cells.

[Filter Hole]

Figure 9:
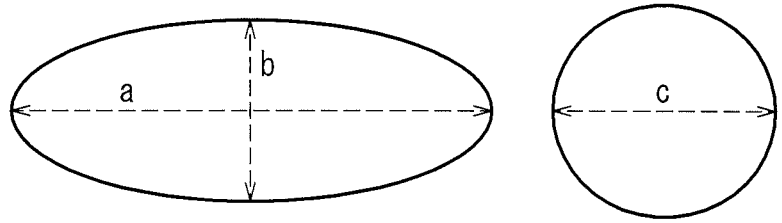
FIG. 9 is a schematic diagram for explaining a hole diameter.

The hole shape of a filter used in the filtration in the processing method of the present disclosure is not particularly limited. In one or more embodiments, the hole shape is selected from the group consisting of a circle, an ellipse, a rectangle, a symmetrical polygon, an asymmetrical polygon, an irregular shape, and a combination of these shapes. In one or more embodiments, the hole shape of the filter is an ellipse with a minor axis diameter of 3.0 μm to 15 μm and a major axis diameter of 1.1 times to 3 times as long as the minor axis diameter, or a shape that contains the ellipse and is in contact with the ellipse on at least two points joining the major axis of the ellipse in terms of improving the capture rate of rare cells. In one or more embodiments, the "shape that contains the ellipse and is in contact with the ellipse on at least two points including both ends of the major axis of the ellipse" may be an ellipse-like shape that is circumscribed about the ellipse so as to touch at least two points including both ends of the major axis of the ellipse, and that is selected from the group consisting of a circle, a rectangle, a symmetrical polygon, an asymmetrical polygon, an irregular shape, and a combination of these shapes. In one or more embodiments of the present disclosure, the major axis or the major axis diameter of a hole indicates the length of the major axis when the hole is elliptical, and the minor axis or the minor axis diameter of a hole indicates the length of the minor axis when the hole is elliptical. If the major axis and the minor axis of a hole are the same, the hole may be circular or may seem to be circular. Unless otherwise noted in the present disclosure, "ϕ a×b" means that the hole shape is an ellipse with a major axis of a μm and a minor axis of b μm, and "ϕ c" means that the hole shape is a circle with a diameter of c μm (see FIG. 9).

In one or more embodiments, the minor axis diameter of the ellipse as a hole of the filter is 3.0 μm or more, 4.0 μm or more, or 5.0 μm or more and 15.0 μm or less, 8.0 μm or less, less than 8.0 μm, 7.5 μm or less, 7.0 μm or less, or 6.5 μm or less in terms of improving the capture rate of small rare cells. In one or more embodiments, the small rare cells are small enough to pass through true circular holes with a diameter of about 10 μm.

In one or more embodiments, the major axis diameter of the ellipse as a hole of the filter is 1.1 times to 3 times, 1.2 times to 2.8 times, or 1.3 times to 2.6 times as long as the minor axis diameter in terms of improving the capture rate of large deformable rare cells and increasing the filter capacity. In one or more embodiments, when the minor axis diameter and the major axis diameter of the ellipse are controlled within the above ranges, respectively, the capture rate of rare cells can be improved by adjusting the filter capacity. The present disclosure is based on this surprising effect. In other words, the capture rate of small rare cells can be maintained by controlling the minor axis diameter of the ellipse within the above range, and the capture rate of deformable rare cells can be improved by extending the ellipse in the major axis direction so as to adjust the filter capacity.

In one or more embodiments, the filter used in the filtration in the processing method of the present disclosure may include holes that do not meet the above requirements as long as the holes do not affect the filtration. Alternatively, in one or more embodiments, the filter may include substantially uniform holes.

[Membrane Filter]

In one or more embodiments, the filter used in the filtration in the processing method of the present disclosure is a membrane filter. In one or more embodiments, the membrane filter includes holes that are in the form of an ellipse with the minor axis diameter and the major axis diameter that fall in the above ranges, respectively, or holes that have a shape that contains the ellipse and is in contact with the ellipse on at least two points joining the major axis of the ellipse in terms of maintaining the capture rate of small rare cells, improving the capture rate of deformable rare cells, and reducing the filtration area. In one or more embodiments, the area of a hole in the membrane filter is 15 $\mu m^2$ to 250 $\mu m^2$, 20 $\mu m^2$ to 150 $\mu m^2$, 30 $\mu m^2$ to 100 $\mu m^2$, or 40 $\mu m^2$ to 80 $\mu m^2$ in terms of maintaining the capture rate of small rare cells, improving the capture rate of deformable rare cells, and reducing the filtration area.

Based on the volume of the blood sample to be processed, the number of the holes in the membrane filter can be defined by "Hole number (holes)=Total volume of blood sample to be processed (nl)/170 to Total volume of blood sample to be processed (nl)/10" or "Total hole area ($\mu m^2$)=Total volume of blood sample to be processed (nl)/3.4 (nl/$\mu m^2$) to Total volume of blood sample to be processed (nl)/0.2 (nl/$\mu m^2$)". In one or more embodiments, the number of the holes is not particularly limited, and can be appropriately set in accordance with the amount of blood per hole in a region through which the sample passes.

When 0.1 ml of blood is processed, the number of the holes may be 600 holes or more, and preferably 900 holes or more, 1200 holes or more, or 1800 holes or more. When 1 ml of blood is processed, the number of the holes may be 6000 holes or more, and preferably 9000 holes or more, 10000 holes or more, 12000 holes or more, or 18000 holes or more. When 5 ml or more of blood is processed, the number of the holes may be 29400 holes or more, and preferably 46000 holes or more, 92000 holes or more, or 178000 holes or more. When 10 ml of blood is processed, the number of the holes may be 61000 holes or more, and preferably 92000 holes or more, 120000 holes or more, 185000 holes or more, or 357500 holes or more. When 100 ml of blood is processed, the number of the holes may be 610000 holes or more, and preferably 920000 holes or more, 1200000 holes or more, or 1850000 holes or more. The number of the holes can be appropriately selected in accordance with the probability of the rare cells being contained in blood. When 1 ml or less of blood is processed, it is desirable that at least 80% of the rare cells can be captured. When the amount of blood is increased to 1 ml or more, the number of the holes may be set so that the capture rate is 80% to 50%.

In one or more embodiments, the membrane filter has a hole density of 300 holes to 40000 holes, 300 holes to 7000 holes, 500 holes to 4000 holes, 700 holes to 4000 holes, 800 holes to 3999 holes, 900 holes to 3900 holes, or 1000 holes to 3900 holes per 1 $mm^2$ in terms of maintaining the capture rate of small rare cells, improving the recovery rate of deformable rare cells, and reducing the filtration area. In one or more embodiments, the membrane filter has a thickness of 1 $\mu m$ to 100 $\mu m$, 1 $\mu m$ to 50 $\mu m$, 1 $\mu m$ to 30 $\mu m$, preferably 1 $\mu m$ to 20 $\mu m$, and more preferably 1 $\mu m$ to 10 $\mu m$.

The shape, number, density, and area of the holes in the membrane filter can be measured, e.g., by an optical microscope, a laser microscope, or an electron microscope. Specifically, they can be measured using the method described in the following example. For example, the hole size can be measured by a laser microscope at an objective lens magnification of 10× to 100×.

In one or more embodiments, the type of the membrane filter used in the filtration in the processing method of the present disclosure is preferably a filter composed of a sheet material having substantially uniform through holes. In this case, any type of the material is available. Examples of the filter include a polycarbonate (PC) filter, a parylene membrane filter, and a metal filter such as nickel (Ni). It is desirable that materials such as plastic, metal, and glass are selected in accordance with a dye or fluorescent staining used for the observation of cells on the filter. A combination of these materials may also be used.

[Filtering Condition]

In one or more embodiments, the filtration in the processing method of the present disclosure is capable of capturing CTCs by introducing blood into a flow path that incorporates the above filter. The filtration is not particularly limited as long as it employs a driving force to transfer a fluid. For example, blood can be introduced into the flow path by applying pressure from the direction of an inlet of the flow path, by reducing pressure from the direction of an outlet of the flow path, or by using a syringe pump or a peristaltic pump. In order to introduce blood into the flow path, e.g., the blood sample is transferred at a flow velocity of 5 $\mu m/min$ to 600 $\mu m/min$ (i.e., at a flow rate of 0.25 nl/min to 30 nl/min) per hole of the filter. Thus, the rare cells can be appropriately captured in a short time compared to the conventional examples.

Under the fluid transfer conditions of the blood sample, the flow velocity is preferably 5 $\mu m/min$ to 600 $\mu m/min$ (i.e., the flow rate is 0.25 nl/min to 30 nl/min), more preferably the flow velocity is 10 $\mu m/min$ to 480 $\mu m/min$ (i.e., the flow rate is 0.5 nl/min to 24 nl/min), even more preferably the flow velocity is 20 $\mu m/min$ to 360 $\mu m/min$ (i.e., the flow rate is 1 nl/min to 18 nl/min), and further preferably the flow velocity is 20 $\mu m/min$ to 120 $\mu m/min$ (i.e., the flow rate is 1 nl/min to 7 nl/min).

There is no particular limitation to a difference in pressure applied to the system of the filter device and the entire flow path (i.e., a pressure difference from the inlet to the outlet of the system) ($\Delta P_1$). The pressure difference is preferably 3.7 kPa or less, more preferably 2.6 kPa or less, and even more preferably 1.3 kPa or less.

Under the fluid transfer conditions of the blood sample, a pressure difference ($\Delta P_2$) between the upper surface and the lower surface of the filter is 110 Pa or less, preferably 100 Pa or less, more preferably 70 Pa or less, 50 Pa or less, and even more preferably 30 Pa or less, 15 Pa or less. In the case of a true circle, a pressure difference is given by $\Delta P_2 = Q \times 8\eta L/(\pi d^4 \times N_0)$, where Q represents the total hole number average flow rate, d represents the radius, L represents the length of the flow path in a hole, $\eta$ represents the viscosity of the fluid to be transferred, $\pi$ represents the ratio of the circumference of a circle to its diameter, and $N_0$ represents the number of the holes. The pressure difference can be determined by a known calculation method based on the hole shape. Blood is a non-Newtonian fluid, and thus the average flow velocity differs depending on the viscosity due to a difference in hematocrit (Hct) even if the pressure difference is the same. Therefore, the average flow velocity has a certain range. When the pressure difference $\Delta P_2$ is set for the use of whole blood, the fluid transfer or pressure may be defined so that the pressure difference $\Delta P_2$ is numerically within the above range using $\eta=4.5$ mPa·S for convenience. If the hematocrit (Hct) of the blood sample is less than 20 because of dilution or the like, the pressure difference $\Delta P_2$ may be set numerically within the above range using $\eta=1$ mPa·S to 2 mPa·S. Alternatively, if the blood sample is diluted to the extent that the effect of the viscosity by plasma or hematocrit (Hct) is not small (e.g., whole blood is diluted 4 to 10 times), the pressure difference $\Delta P_2$ may be calculated in accordance with the viscosity of the diluted fluid. When the flow rate is constant by using a syringe pump or the like, the blood sample may be transferred so that the pressure difference $\Delta P_2$ is within the above range. The above fluid transfer conditions can be accomplished by a mechanism that can transfer a fluid at constant pressure or a mechanism that can transfer a fluid at a constant flow rate, which are well known to those skilled in the art.

[Method for Separating or Detecting Rare Cell in Sample Containing Blood Component]

As a result of the filtration in the processing method of the present disclosure, rare cells (if any) remain on the filter after the sample containing blood components has been filtered, so that the rare cells can be separated or detected. Therefore, in another aspect, the present disclosure relates to a method for separating or detecting rare cells in a sample containing blood components, which includes separating or detecting rare cells by processing a blood sample by the processing method of the present disclosure.

[Labeling Process of Rare Cell in Blood]

In the processing method of the present disclosure, a labeling process of rare cells in blood may be performed either before, in parallel with, or after the separation of the rare cells. The labeling of rare cells is useful not only for the separation or detection method of the present disclosure, but also for a CTC enumeration method, as will be described later. Moreover, the labeling of rare cells may be useful for the analysis of the rare cells after the separation. Therefore, in one or more embodiments, the processing method of the present disclosure includes the labeling process. The labeling of rare cells is useful for a CTC enumeration method, as will be described later, and may also be useful for the analysis of the rare cells after the separation. Therefore, in one or more embodiments, the separation or detection method of the present disclosure includes the labeling process.

The labeling process can be performed, e.g., by bringing a known labeling reagent into contact with the rare cells. Typically, the labeling reagent may be mixed with the blood sample. The labeling is not particularly limited. In one or more embodiment, examples of the labeling include radioactive labeling, fluorochrome labeling, dye staining or labeling, magnetic labeling, charge labeling, and a combination of these processes, and each of them may use a suitable labeling reagent.

In other words, the labeling process of rare cells can be performed by a labeling method associated with a detection method selected from the group consisting of a detection method using a radioactive substance, a detection method using a luminous phenomenon, a detection method using a dye, a detection method using magnetic properties, an electrical detection method, an optical detection method, and a combination of these methods.

In the processing method of the present disclosure, the separation or detection of rare cells can also be achieved by detecting a change in the filter electrically, gravimetrically, or optically.

[Method for Analyzing Rare Cell in Sample Containing Blood Component]

In another aspect, the present disclosure relates to a method for analyzing rare cells in a sample containing blood components, which includes separating or detecting rare cells by the separation or detection method of the present disclosure, and then analyzing the rare cells by a method including kinetic observation or activity measurement of the rare cells. In the present disclosure, since the cells can be captured alive, the rare cells can be separated or detected by the separation or detection method of the present disclosure, and then analyzed by the method including kinetic observation or activity measurement of the rare cells.

[Method for Enumerating CTC]

It has been reported that there is a relationship between the number of CTCs in blood and metastasis and prognosis of cancer. Many studies have been conducted to find indicators of diagnosis, prognosis, and the prediction or evaluation of a therapeutic effect of cancer, and the enumeration of CTCs in blood has been known. The processing method and/or the separation or detection method of the present disclosure can separate CTCs (rare cells) while suppressing damage to the CTCs. Moreover, the nucleic acids of CTCs may be measured. Therefore, in another aspect, the present disclosure relates to a method for enumerating CTCs in a blood sample, which includes separating or detecting rare cells by processing the blood sample by the processing method of the present disclosure and/or separating CTCs from the blood sample by the separation or detection method of the present disclosure. The enumeration of CTCs or the measurement of the nucleic acids of CTCs may be performed, e.g., by flow cytometry at the same time as the separation after appropriate labeling, or by observing and counting the separated cells under a microscope, or by using the fluorescent values in view of the morphology or the amount of DNA or RNA of cancer cells.

[Filter]

In yet another aspect, the present disclosure relates to a filter used in the processing method, the separation or detection method, and/or the CTC enumeration method of the present disclosure. The filter includes holes with a hole density of at least 200 holes/mm$^2$ to 40000 holes/mm$^2$, wherein the holes are in the form of an ellipse with a minor axis diameter of 3.0 μm to 15 μm and a major axis diameter of 1.1 times to 3 times as long as the minor axis diameter, or the holes have a shape that contains the ellipse and is in contact with the ellipse on at least two points joining the major axis of the ellipse. The hole shape or the like of the filter of the present disclosure is the same as those of the filter used in the processing method of the present disclosure.

[Device for Capturing Rare Cell]

In yet another aspect, the present disclosure relates to a device for capturing rare cells that captures rare cells in a sample. In one or more embodiments, the device for capturing rare cells of the present disclosure includes an inlet, an outlet, and a flow path connecting the inlet and the outlet, wherein a separation portion that includes a filter holder for holding the filter of the present disclosure is provided in a position corresponding to a part of the flow path. The device for capturing rare cells of the present disclosure can use the filter of the present disclosure to perform the method for processing a blood sample of the present disclosure.

The present disclosure can relate to the following one or a plurality of embodiments.

<1> A method for separating or detecting rare cells in a blood sample using a filter including holes with a hole density of 200 holes/mm² to 40000 holes/mm², wherein the holes are in the form of an ellipse with a minor axis diameter of 3.0 µm to 15 µm and a major axis diameter of 1.1 times to 3 times as long as the minor axis diameter, or the holes have a shape that contains the ellipse and is in contact with the ellipse on at least two points including both ends of the major axis of the ellipse, the method comprising:
separating or detecting rare cells by filtering the blood sample so that a filter capacity per hole of the filter is 6 µl/hole or less expressed in terms of blood.

<2> The method according to <1>, wherein the blood sample is filtered in a volume of 1 µl/hole or less expressed in terms of blood with respect to a hole of the filter.

<3> The method according to <1> or <2>, wherein the blood sample is filtered in a volume of 0.2 µl/hole or less expressed in terms of blood with respect to a hole of the filter.

<4> The method according to any one of <1> to <3>, wherein the filter has a hole density of 300 holes/mm² to 7000 holes/mm².

<5> The method according to any one of <1> to <4>, wherein the filter has a hole density of 300 holes/mm² to 5000 holes/mm².

<6> The method according to any one of <1> to <5>, wherein the filter has a hole density of 500 holes/mm² to 4000 holes/mm².

<7> The method according to any one of <1> to <6>, wherein the filter has a hole density of 800 holes/mm² to 4000 holes/mm².

<8> The method according to any one of <1> to <7>, wherein the holes are in the form of an ellipse with a minor axis diameter of 4.0 µm to 10 µm and a major axis diameter of 1.1 times to 3 times as long as the minor axis diameter, or the holes have a shape that is in contact with the ellipse on at least two points including both ends of the major axis of the ellipse.

<9> The method according to any one of <1> to <8>, wherein an area of a hole in the filter is 15 µm² to 250 µm².

<10> The method according to any one of <1> to <9>, wherein the area of a hole in the filter is 20 µm² to 100 µm².

<11> The method according to any one of <1> to <10>, wherein the area of a hole in the filter is 25 µm² to 80 µm².

<12> The method according to any one of <1> to <11>, wherein the holes are in the form of an ellipse with a minor axis diameter of 5.0 µm to 8 µm and a major axis diameter of 1.1 times to 3 times as long as the minor axis diameter, or the holes have a shape that is in contact with the ellipse on at least two points including both ends of the major axis of the ellipse.

<13> The method according to any one of <1> to <12>, comprising:
separating or detecting rare cells by filtering the blood sample so that the filter capacity with respect to the holes in the filter is defined by "Total volume of blood sample to be processed (nl)=Hole number (holes)×10 to Hole number (holes)×170" or "Total volume of blood sample to be processed (nl)=Total hole area (µm²)×0.2 (nl/µm²) to Total hole area (µm²)×3.4 (nl/µm²)", expressed in terms of blood.

<14> The method according to any one of <1> to <13>, comprising:
separating or detecting rare cells by processing the blood sample in an amount indicated by "Total volume of blood sample to be processed (a" using a filter in which a number of the holes is defined by "Hole number (holes)=Total volume of blood sample to be processed (nl)/170 to Total volume of blood sample to be processed (nl)/10" or a total area of the holes is defined by "Total hole area (µm²)=Total volume of blood sample to be processed (nl)/3.4 (nl/µm²) to Total volume of blood sample to be processed (nl)/0.2 (nl/µm²)".

<15> The method according to any one of <1> to <14>, comprising:
separating or detecting rare cells by filtering the blood sample so that the filter capacity per hole of the filter is 10 nl/hole to 108 nl/hole expressed in terms of blood.

<16> The method according to any one of <1> to <15>, wherein the blood sample is filtered in a volume of 0.1 µl/hole or less expressed in terms of blood with respect to a hole of the filter.

<17> The method according to any one of <1> to <16>, wherein the blood sample is filtered in a volume of 0.06 µl/hole or less expressed in terms of blood with respect to a hole of the filter.

<18> The method according to any one of <1> to <17>, wherein a number of the holes in the filter is more than 10000 holes.

<19> The method according to any one of <1> to <18>, wherein as a fluid transfer condition for filtration, pressure is set so that blood is transferred at a flow velocity of 5 µm/min to 600 µm/min per hole.

<20> The method according to any one of <1> to <19>, wherein as a fluid transfer condition for filtration, pressure is set so that blood is transferred at 0.05 nl/min to 30 nl/min per hole.

<21> The method according to any one of <1> to <20>, wherein the blood sample is transferred so that a pressure difference between an upper surface and a lower surface of the filter during filtration is 4 Pa to 110 Pa.

<22> The method according to any one of <1> to <21>, wherein the filter is made of at least one selected from the group consisting of glass, plastic, metal, and a combination thereof.

<23> The method according to any one of <1> to <22>, wherein the rare cells are selected from the group consisting of cancer cells, circulating tumor cells, vascular endothelial cells, vascular endothelial precursor cells, cancer stem cells, epithelial cells, hematopoietic stem cells, mesenchymal stem cells, embryonal cells, and a combination thereof.

<24> A method for analyzing rare cells in a blood sample comprising:
separating or detecting rare cells by the method according to any one of <1> to <23>, and then
analyzing the rare cells by a method including kinetic observation or activity measurement of the rare cells.

<25> A filter used in the method according to any one of <1> to <24>, comprising holes with a hole density of at least 200 holes/mm² to 40000 holes/mm²,
wherein the holes are in the form of an ellipse with a minor axis diameter of 3.0 µm to 15 µm and a major axis diameter of 1.2 times to 3 times as long as the minor axis diameter, or the holes have a shape that is in contact with the ellipse on at least two points including both ends of the major axis of the ellipse.

<26> A filter used in the method according to any one of <1> to <24>, comprising more than 10000 holes,
wherein the filter allows 1 ml to 5 ml of blood to be processed.

<27> A filter used in the method according to any one of <1> to <24>, comprising 29000 holes or more,
wherein the filter allows 5 ml to 10 ml of blood to be processed.

<28> A filter used in the method according to any one of <1> to <24>, comprising 60000 holes or more, wherein the filter allows more than 10 ml of blood to be processed.

<29> A device for capturing rare cells that captures rare cells in a sample, comprising:
   an inlet;
   an outlet; and
   a flow path connecting the inlet and the outlet,
   wherein a separation portion that includes the filter according to any one of <25> to <28> and a filter holder is provided in a position corresponding to a part of the flow path.

EXAMPLES

Hereinafter, the present disclosure will be described in more detail by way of examples, which are for illustrative purposes only, but the present disclosure is not limited to the examples.

Using the filters and the fluid transfer conditions shown in Table 1 and FIG. 1, the method for processing a blood sample was performed.

counted or the number of holes per area was determined with a microscope, and then the filtration area to be used was calculated.

(Method for Preparing Cancer Cell)

According to the ordinary method, human mammary epithelial cancer cells (cell line name: MCF-7), human colon adenocarcinoma cells (cell line name: SW620), human prostate cancer cells (cell line name: PC3-9), human alveolar epithelial cancer cells (cell line name: NCI-H358), human gastric cancer cells (cell line name: MKN-7), and sarcoma (HT-1080) were cultured in petri dishes. After removal of the supernatant, each culture medium was washed with PBS (−), and the supernatant was further removed. Then, the cells were treated with trypsin (Invitrogen) at 37° C. for 3 minutes, suspended in a culture medium including serum, and placed in a 15 ml centrifuge tube. The cells were centrifuged with a centrifuge (CR20F: Hitachi, Ltd.) to remove the supernatant. Subsequently, the cells were resuspended in a culture medium including serum and collected. A human gastric cancer cell line (cell line name: SNU-1) and

TABLE 1

| | | | Filter | | | | | | |
|---|---|---|---|---|---|---|---|---|---|
| Shape | Major axis diameter/ Minor axis diameter | Hole area μm² | Pitch between centers of holes | Hole density hole/mm² | Opening ratio per area (%) | Thickness | Material | Filtration area mm² | Total hole number |
| Circle | 8 × 8 | 50 | 19 × 14 | 3759 | 19 | 5 μm | nickel (metal) | 20 | 73816 |
| Ellipse | 9.8 × 6.5 | 50 | 19 × 14 | 3759 | 19 | 5 μm | nickel (metal) | 20 | 73816 |
| Ellipse | 12.8 × 5 | 50 | 19 × 14 | 3759 | 19 | 5 μm | nickel (metal) | 20 | 73816 |
| Ellipse | 8 × 6.5 | 41 | 19 × 14 | 3759 | 15 | 5 μm | nickel (metal) | 20 | 73816 |
| Circle | 6.5 × 6.5 | 33 | 19 × 14 | 3759 | 12 | 5 μm | nickel (metal) | 20 | 73778 |
| Ellipse | 8 × 5 | 31 | 19 × 14 | 3759 | 12 | 5 μm | nickel (metal) | 20 | 73778 |
| Circle | 5 × 5 | 20 | random | 3534 | 8 | 8 μm | PC (resin) | 20 | 69390 |
| Circle | 4 × 4 | 13 | 19 × 19 | 2770 | 3 | 5 μm | nickel (metal) | 20 | 54390 |

| | Filtration conditions | | |
|---|---|---|---|
| | Blood flow rate per hole in transfer of 8 ml blood nl/min | Pressure $P_1$ in entire system (inlet − outlet) during blood filtration kPa | Pressure $P_1$ in entire system (inlet − outlet) during washing filtration kPa |
| | 4~7 nl/min | 1.3 kPa ± 0.1 | 0.4 kPa ± 0.1 |
| | 4~7 nl/min | 1.3 kPa ± 0.1 | 0.4 kPa ± 0.1 |
| | 4~7 nl/min | 1.3 kPa ± 0.1 | 0.4 kPa ± 0.1 |
| | 4~7 nl/min | 1.3 kPa ± 0.1 | 0.4 kPa ± 0.1 |
| | 4~7 nl/min | 1.3 kPa ± 0.1 | 0.4 kPa ± 0.1 |
| | 4~7 nl/min | 1.3 kPa ± 0.1 | 0.4 kPa ± 0.1 |
| | clogging | 1.3 kPa ± 0.1 | 0.4 kPa ± 0.1 |
| | clogging | 1.3 kPa ± 0.1 | 0.4 kPa ± 0.1 |

Filters were produced by designing the pitch in the major axis direction and the pitch in the minor axis direction of various holes. A polycarbonate track-etched membrane with a hole diameter of φ 5 μm or φ 8 μm (manufactured by GE Healthcare Japan Corporation) was used as a plastic filter. The hole diameter of the filters can be measured, e.g., by a pore size distribution evaluation apparatus using a bubble point method or a mercury intrusion method, or by a known measurement method with an optical microscope such as a fluorescence microscope, a laser microscope, or an electron microscope. Specifically, the number of holes was directly a human colon adenocarcinoma cell line (cell line name: SNU-C1), both of which were suspended, were placed in 15 ml centrifuge tubes without the trypsin treatment. Some of human colon adenocarcinoma cells (cell line name: Colo320DM) adhered to suspended cells. Therefore, suspended cells were placed in a 15 ml centrifuge tube, while the cells adhered to the suspended cells were treated with trypsin in the same manner as the other adherent cells, and then placed in the 15 ml centrifuge tube. The cells were centrifuged, suspended in a culture medium including serum, and collected.

(Preparation of Cell Count)

As cancer cell samples, SNU-1, MKN-7, MCF-7, SW620, Colo320DM, SNU-C1, PC3-9, NCI-H358, and HT-1080, which were derived from gastric cancer cells, breast cancer cells, colon cancer cells, prostate cancer cells, lung cancer cells, and sarcoma and were previously stained, were prepared to have any number of cells such as $0.5 \times 10^5$ cells/ml or $1 \times 10^5$ cells/ml. The SNU-1 cells were used as a model of deformable cells, since they easily passed through 8 µm holes compared to the other cell suspensions. The SW620 cells were used as a model of small cells, since they were the smallest in the above cells. The deformability of the cells was evaluated in the following manner. Using a track-etched membrane (polycarbonate (PC), circular hole: φ 8 µm, filtration size: φ 10 mm), a cell suspension containing an excessive number of the cells, which was more than the number of the holes in the membrane, was supplied and clogged the membrane. Then, a negative pressure was created in an airtight bottle that was located under the filter and communicated with the discharge flow path. At this time, when the clogging was eliminated and the cell suspension started to flow swiftly, the cells with relatively low pressure were selected as highly deformable cells (see Table 2).

TABLE 2

| | SNU-1 | SW620 | HT-1080 | NCI-H358 | PC3-9 | MCF-7 |
|---|---|---|---|---|---|---|
| Pressure (kPa) at the time of eliminating clogging of filter with cells | 0.6-1 | 3.5 | 2-2.2 | 6.5-6.7 | 3.5-3.8 | 5-8 |

(Capturing Process of Rare Cell)

Figure 2:
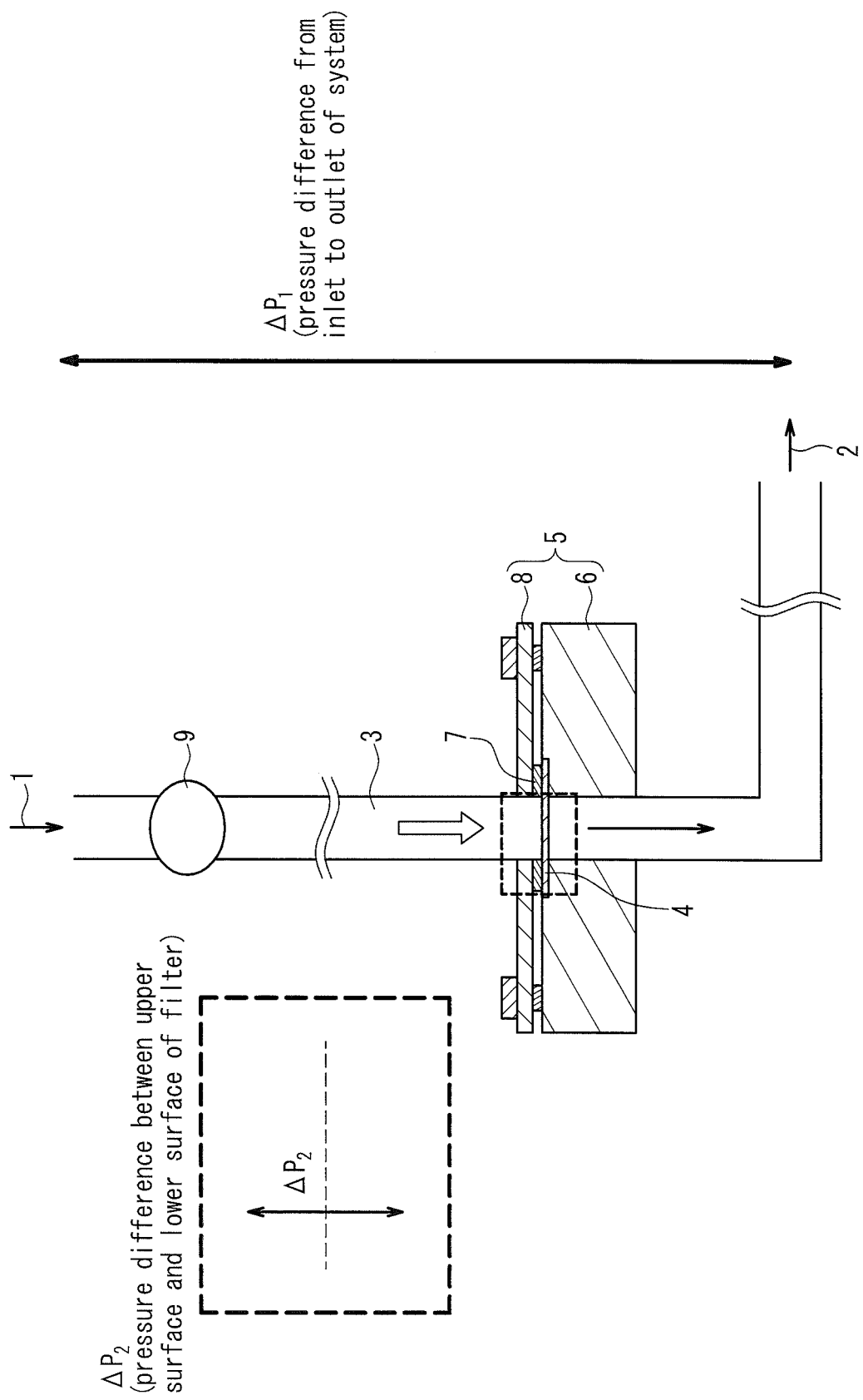
FIG. 2 is a schematic diagram of a device for capturing rare cells.

Cell separation experiments were conducted using a device for capturing rare cells shown in FIG. 2.

The device includes an inlet 1 for supplying a sample, a cleaning fluid, a stain solution, or the like to a filter, an outlet 2, and a flow path 3 connecting the inlet 1 and the outlet 2. A separation portion that includes a filter 4 and a filter holder 5 for holding the filter 4 is provided in a position corresponding to a part of the flow path 3. Specifically, the filter 4 is disposed on a base 6, an O ring 7 is put on the upper surface of the filter 4, and a cover 8 is placed to fix the separation portion, thus producing a filter device including holes, as shown in Table 1. In this example, a plurality of filters having a filtration area of 5 mm² to 80 mm² were used. A connection portion and a three way stopcock that allows the flow of a fluid to be switched were attached to the upper portion of the filter device, and the flow path was formed by a Safeed extension tube (manufactured by Terumo Corporation). The inlet 1 was located at the end of the flow path 3 that was opposite to the filter 4, and a pressure means 9 was provided between the inlet 1 and the filter 4 (as a mechanism that can transfer a fluid at constant pressure or a mechanism that can transfer a fluid at a constant flow rate). The fluid transfer conditions were set by adjusting the filtration pressure or using a syringe pump. The discharge flow path was formed by coupling the Safeed extension tube to a tube with an inner diameter of 2 mm, and the outlet 2 was located at the end of this tube.

(Setting Transfer Condition)

The flow path was filled with PBS (−) (composition: 1 L distilled water containing 8000 mg of sodium chloride, 200 mg of potassium chloride, 1150 mg of sodium monohydrogen phosphate (anhydrous), and 200 mg of potassium dihydrogen phosphate (anhydrous)). By adjusting the pressure or using a syringe pump, blood was filtered at 30 nl/min or less (i.e., 600 µm/min or less) per hole of the filter. After the separation of the cancer cells from the blood, the flow path was washed with PBS (−) at about 1000 µl/min (14 nl/min per hole). Table 7 shows the relationship between the flow rate and each of φ 8 µm holes and φ 9.8×6.5 µm holes. Based on the results in Table 7, the flow rate per hole was set to be 4 nl/min to 7 nl/min when the filtration pressure in the entire system was 1.3 kPa±0.1 or the amount of blood per hole was 108 nl. Such filtration conditions were regarded as basic conditions. A comparison between the filters was performed under the basic conditions at the same pressure. The conditions were appropriately set in accordance with the number of the holes.

(Performing Sample Processing)

A part of blood (white blood cell count: 3000 to 10000 cells/µl) that had been drawn into a blood collection tube (EDTA-2K) was placed in a syringe, and then 10 µl of cancer cell suspension with a desired concentration was added to the blood in the syringe. Subsequently, the residual blood was added and mixed, so that a blood sample was prepared. When this blood sample was supplied to the inlet of the device for capturing rare cells, the pressure means applied pressure shown in the following Table 4 so as to meet the fluid transfer conditions for each hole of the filter, and thus the blood sample was filtered. After completion of the filtration, the device was washed with PBS (−), and the three way stopcock and the connection portion, which were connected to the portion above the separation portion, were slowly removed. Then, a glass slide was gradually put on the filter and an observation plane was formed. This was placed in a fluorescence microscope, and fluorescent stained cancer cells remaining on the filter were enumerated. The cancer cells recovered by the processing of this example were able to be cultured.

In the above processing, the cancer cells were stained in the following manner. The prepared cancer cells were collected from the culture medium, and then centrifuged with a centrifuge (CR20F: Hitachi, Ltd.) at 1500 rpm at room temperature (24° C.) for 3 minutes. After removal of the supernatant, PBS (−) was added to suspend the cells. The cells suspended in PBS (−) were fluorescent stained. In this case, CellTracker (Invitrogen) was used as a fluorescent dye. The CellTracker (Invitrogen) is a reagent that can diffuse through the cell membrane of live cells, and reacts with an intracellular substance and is converted into a fluorescent substance.

The CellTracker was dissolved in DMSO to 10 mM and used so that the final concentration in the reaction was 0.5 µM to 0.25 µM. The CellTracker was allowed to react in PBS (−) for 30 to 40 minutes. The cancer cells were appropriately stained with CellTracers that emit green fluorescence (CellTracker Green CMFDA), orange fluorescence (CellTracker Orange CMRA), and blue fluorescence (CellTracker Blue CMF2HC).

The recovery rate of cancer cells was calculated in the following manner. A cancer cell suspension was added to blood and filtered. Then, the fluorescent stained cancer cells on the filter surface were counted. On the other hand, the cancer cell suspension was added to a microplate well in the same amount as that added to the blood, and the number of the cancer cells was counted by a fluorescence microscope. The capture rate was calculated, where the number of the cells in the microplate well was used as a denominator and the number of the cells remaining on the filter was used as a numerator.

(Cell Staining and Activity on Filter)

PC3 cells were processed in the above manner except that the PC3 cells were not previously stained with the Cell-Tracker. After the PC3 cells were separated from blood, 1 mM 5-aminolevulinic acid (ALA) prepared with PBS was added from the inlet and allowed to react with the PC3 cells. Then, fluorescent staining was performed by the conversion and accumulation of protoporphyrin IX due to ALA metabolism using the activity of the enzyme in the PC cells on the filter. In addition, white blood cells were stained with an antibody against CD45 or the like, and hoechst (which can stain even live cells) was used to stain nuclei to be examined. Consequently, 81% of the PC3 cells were observed to emit fluorescence derived from the protoporphyrin IX, and the activity was confirmed. In the cancer cells, the protoporphyrin IX (red fluorescent substance) may be produced immediately before it is metabolized into heme, since metabolism is suppressed in the synthetic and metabolic pathway of heme that is used in the citric acid cycle. With this method, it is known that 5-aminolevulinic acid (ALA), which is a precursor of protoporphyrin IX, is added to cancer cells so that the protoporphyrin IX (red fluorescent substance) is accumulated, and thus the fluorescent stained cancer cells can be specifically detected.

Tables 3 to 9 show the results of the capturing process of rare cells.

Tables 3 to 7 confirm that when a blood sample is processed with the filter capacity of the present disclosure by controlling the hole shape, a predetermined hole area, the amount of blood per hole, and the blood flow rate per hole, instead of simply reducing the hole diameter, small cells and deformable cells can be captured alive. Moreover, as can be seen from Table 8, it is surprising that the effect of capturing the deformable cells can be achieved no matter how the filtration area, the hole density, the number of the holes, and the amount of the blood sample are different.

Table 8 shows data indicating the differences in the number of the holes, the hole density, the filtration area, and the amount of blood to be processed.

Example 1

Figure 3:
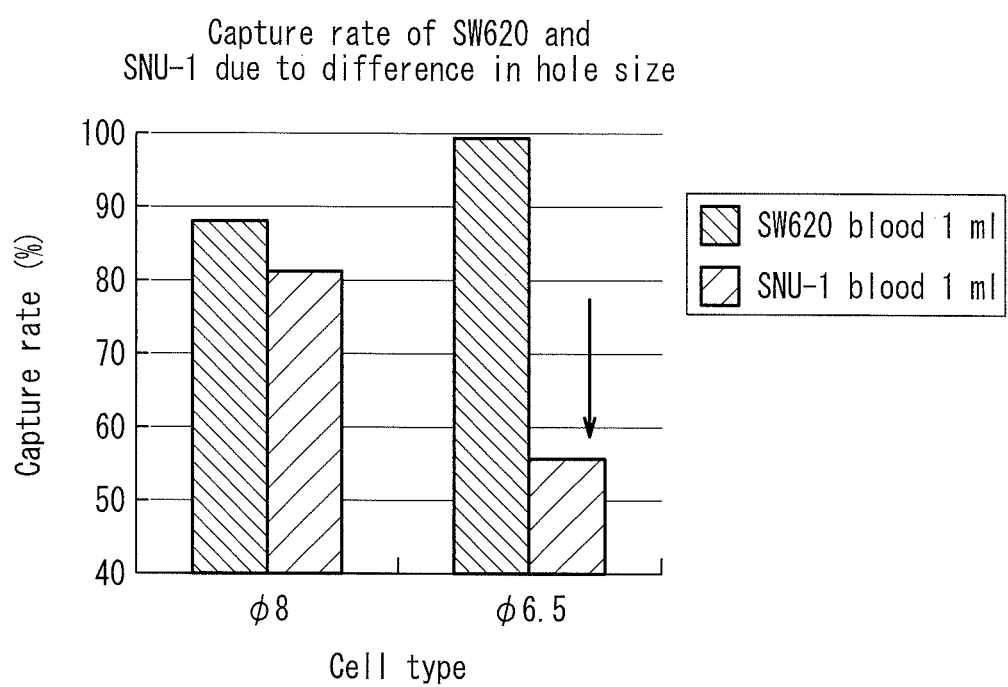
FIG. 3 shows the influence on the capture rate of cells due to a difference in the hole area.

In the following examples, using filters having the same number of holes and the same filtration area, blood samples were processed in a volume of 14 nl per hole (the total volume of the blood sample to be processed: 1 ml). Consequently, the recovery rate of small cells that would pass through 10 μm holes was generally high as long as the holes were smaller than the cells regardless of the hole shape. On the other hand, the recovery rate of deformable cancer cells was low when the holes were small. Table 3 and FIG. 3 show data comparing the capture capabilities of various holes among the filters. In this case, the total volume of the blood sample to be processed was 1 ml. As shown in Table 3, whether the hole shape was a true circle or an ellipse, the capture rate of deformable cancer cells was significantly reduced as the hole area became smaller. Moreover, clogging (blockage) occurred in ϕ 4 μm holes before the blood sample in a volume of 14 nl/hole had reached the total volume of the blood sample to be processed. Thus, a small hole area had adverse effect particularly on the capture rate of deformable cells. In this regard, since the capture rate was improved by extending the major axis, it was confirmed that the problem of the capture rate of deformable cells could not be solved only by reducing the hole diameter. Further, as described in the above documents, small cancer cells that would pass through ϕ 10 μm holes or ϕ 11 μm holes can also be captured by shortening the minor axis, e.g., an ellipse of ϕ 12.7 μm×ϕ 5 μm. If the hole area is at least 33 μm² or more, the capture rate of deformable cells can be improved whether the hole shape is a true circle or an ellipse.

TABLE 3

<Small cancer cells>

| SW620 | Hole area μm² | Amount of blood per hole 14 nl | Total volume of blood sample processed |
|---|---|---|---|
| ϕ8 | 50 | 92% | 1 ml |
| ϕ9.8 × 6.5 | 50 | 95% | 1 ml |
| ϕ12.7 × 5 | 50 | 103% | 1 ml |
| ϕ8 | 41 | 89% | 1 ml |
| ϕ6.5 | 33 | 100% | 1 ml |
| ϕ8 × 5 | 31 | 91% | 1 ml |
| ϕ5 | 20 | 84% | 0.971 ml |
| ϕ4 | 13 | clogging | 0.776 ml |

<Highly deformable cells>

| SNU-1 | Hole area μm² | Amount of blood per hole 14 nl | Total volume of blood sample processed |
|---|---|---|---|
| ϕ8 | 50 | 91% | 1 ml |
| ϕ9.8 × 6.5 | 50 | 95% | 1 ml |
| ϕ12.7 × 5 | 50 | 101% | 1 ml |
| ϕ8 × 6.5 | 41 | 83% | 1 ml |
| ϕ6.5 | 33 | 56% | 1 ml |
| ϕ8 × 5 | 31 | 41% | 1 ml |
| ϕ5 | 20 | 57% | 0.971 ml |
| ϕ4 | 13 | clogging | 0.776 ml |

Example 2

Figure 4:
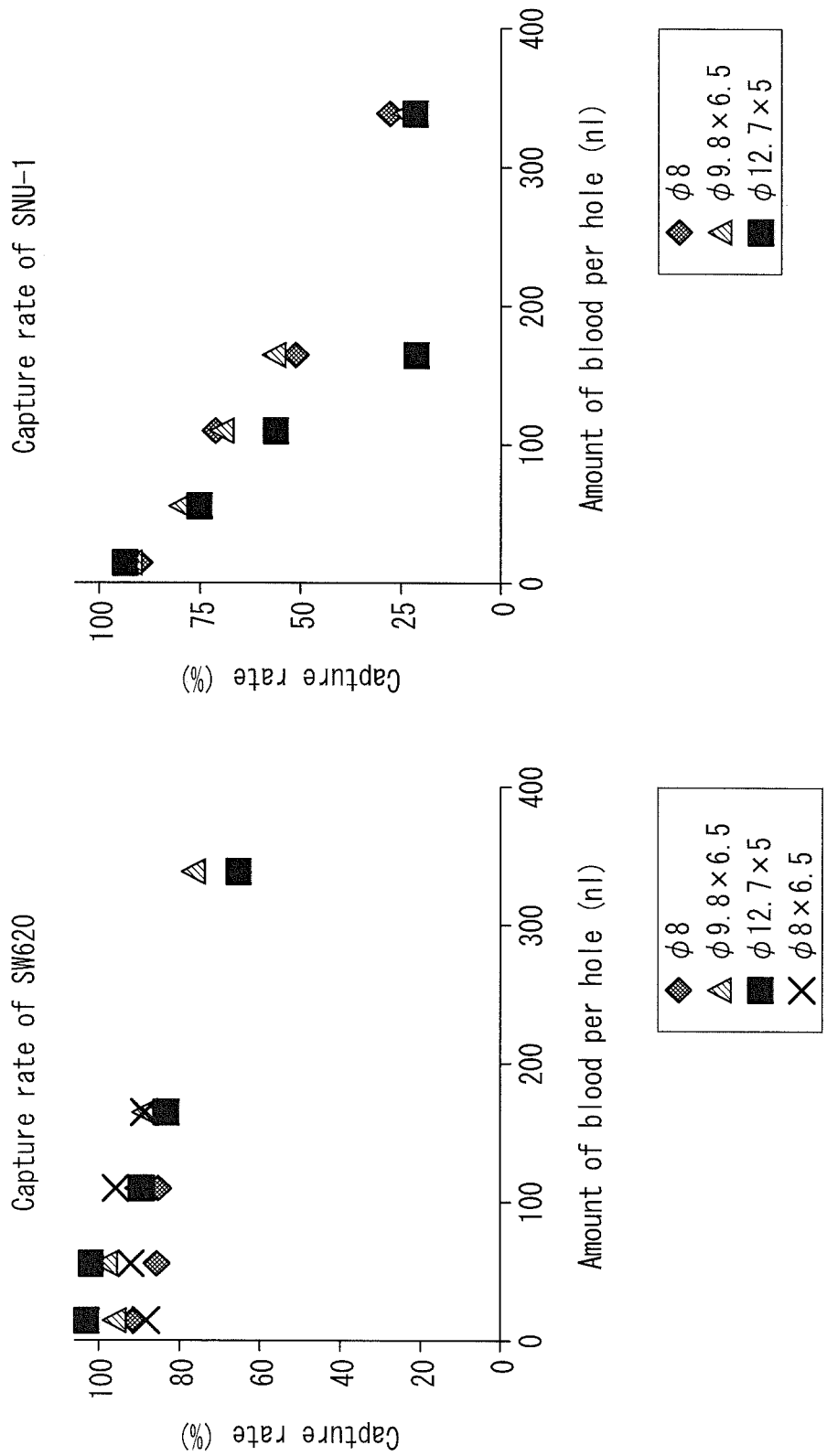
FIG. 4 shows the influence on the capture rate of cells due to a difference in the filter capacity of a blood sample per hole.

The amount of a blood sample to be processed through each of the filters was considered. If a large amount of blood can be processed with the same filtration area, it is possible to reduce the filtration area of the filter to be used, to suppress the bulk of the filtration portion in the device, and to ensure cost effectiveness, as compared to the conventional examples. Tables 4 and 5 show average data of the capture rates of SW620 cells and SNU-1 cells, respectively. The average data are also plotted in FIG. 4. In this case, the ϕ 8 filter, the ϕ 9.8×6.5 filter, and the ϕ 12.7×5 filter were used, each of which achieved a better capture rate for 1 ml of blood, and the amount of the blood sample to be processed was increased up to 25 ml. Surprisingly, when the filtration area was 20 mm², these filters continued to process blood without clogging (blockage) until 25 ml (filtration time: 50 min to 70 min). Thus, a high capture rate of small cancer cells was maintained (see Table 4). On the contrary, the ϕ 5 filter caused clogging.

TABLE 4

<Small cancer cells>

| SW620 | Amount of blood per hole (nl) | | | | |
|---|---|---|---|---|---|
| | 14 | 54 | 108 | 163 | 339 |
| | Capture rate | | | | |
| φ8 | 92% | 86% | 86% | 86% | 66% |
| φ9.8 × 6.5 | 96% | 99% | 91% | 89% | 77% |
| φ12.7 × 5 | 103% | 102% | 90% | 84% | 67% |
| φ8 × 6.5 | 89% | 92% | 96% | 89% | |
| φ6.5 | 100% | 93% | 101% | | |
| φ8 × 5 | 91% | | | | |
| Total volume of blood sample processed | 1 ml | 4 ml | 8 ml | 12 ml | 25 ml |
| φ5 | 84% | — | clogging | — | — |
| Total volume of blood sample processed | 0.971 ml | | 6.9 ml | | |
| φ4 | clogging | — | clogging | — | — |
| Total volume of blood sample processed | 0.776 ml | | 6 ml | | |

Figure 5:
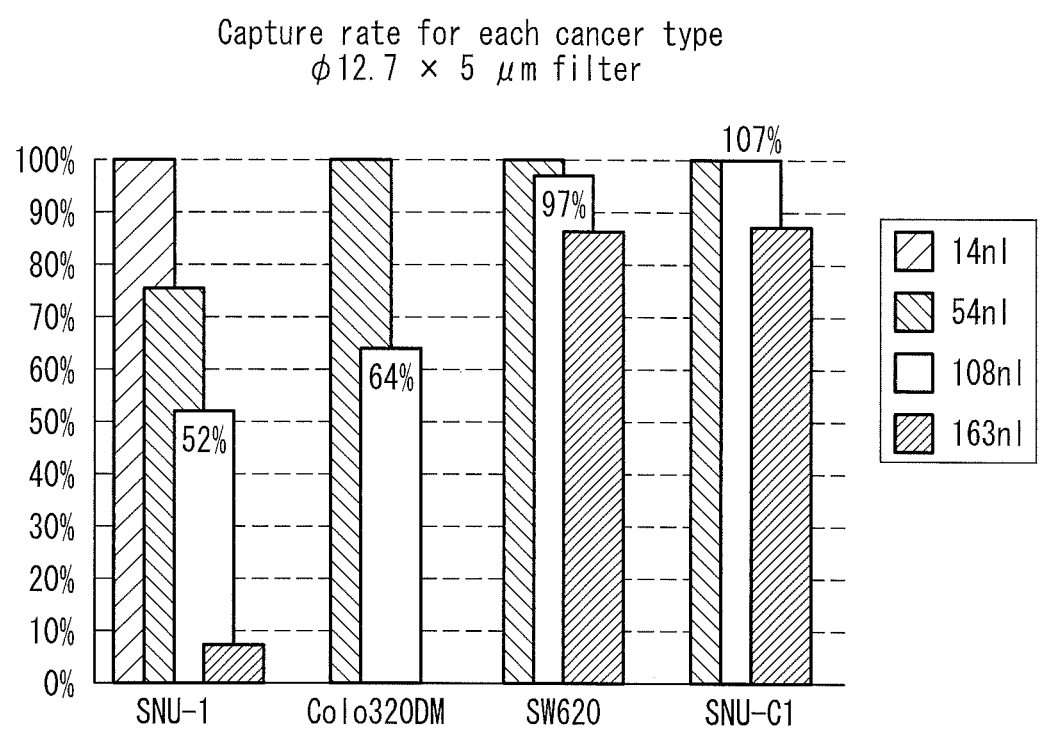
FIG. 5 shows the tendency of the capture rate to decrease with an increase in the amount of blood to be processed regardless of the types of filters or the types of cells.

Since the SW620 cells were little affected by the amount of blood, the capture capabilities were maintained. However, the capture rate of the SNU-1 cells, which were relatively deformable cancer cells, was reduced with an increase in the amount of blood (see Table 5). If blood is filtered by relying solely on the cell size without taking into account the amount of the blood sample to be processed per hole, the capture capabilities cannot be obtained from blood containing deformable cancer cells. The present inventor found that there is an appropriate amount of the blood sample to be processed with respect to the number of the holes, even if no clogging (blockage) occurs, when the rare cells are to be captured. Moreover, the present inventor found that a high capture rate of deformable cells can be achieved by appropriately setting the number of the holes and the amount of the blood sample to be processed per hole in the range of 10 nl to 170 nl in view of the capture rate and the amount of the blood sample to be processed. The capture rates for each of the filters with different holes are plotted in FIG. 4. The tendency of the capture rate to decrease with an increase in the amount of blood was more or less confirmed regardless of the types of cells or the types of filters (see Table 6 and FIG. 5).

TABLE 5

<Highly deformable cells>

| SNU-1 | Amount of blood per hole (nl) | | | | |
|---|---|---|---|---|---|
| | 14 | 54 | 108 | 163 | 339 |
| | Capture rate | | | | |
| φ8 | 91% | 77% | 72% | 52% | 28% |
| φ9.8 × 6.5 | 93% | 81% | 71% | 57% | 25% |
| φ12.7 × 5 | 95% | 76% | 57% | 21% | 22% |
| φ8 × 6.5 | 83% | 74% | 61% | 39% | |
| φ6.5 | 56% | 46% | 29% | | |
| φ8 × 5 | 41% | 47% | 31% | | |
| Total volume of blood sample processed | 1 ml | 4 ml | 8 ml | 12 ml | 25 ml |
| φ5 | 57% | — | clogging | — | — |
| Total volume of blood sample processed | 0.971 ml | | 6.9 ml | | |
| φ4 | clogging | — | clogging | — | — |
| Total volume of blood sample processed | 0.776 ml | | 6 ml | | |

TABLE 6

| COLO320 | Amount of blood per hole (nl) | |
|---|---|---|
| | 54 nl | 108 nl |
| Type of filter | Capture rate | |
| φ8 | 100% | 84% |
| φ9.8 × 6.5 | 93% | 77% |
| φ12.7 × 5 | 101% | 64% |
| φ8 × 6.5 | 97% | 77% |
| φ6.5 | 73% | 37% |
| φ8 × 5 | 43% | 58% |
| Total volume of blood sample processed | 4 ml | 8 ml |

| <φ12.7 × 5 filter> | Amount of blood per hole (nl) | | | |
|---|---|---|---|---|
| Type of cell | 14 nl | 54 nl | 108 nl | 163 nl |
| | Capture rate | | | |
| SNU-1 | 101% | 76% | 52% | 22% |
| Colo320DM | | 101% | 64% | |
| SW620 | | 102% | 97% | 87% |
| SNU-C1 | | 117% | 107% | 87% |
| Total volume of blood sample processed | 1 ml | 4 ml | 8 ml | 12 ml |

Example 3

Next, data of the capture rates of cells when the filtration pressure was varied during filtration will be shown in the following. In general, high pressure would make it easy for cells to pass through the holes of a filter, and thus degrade the capture capabilities, and low pressure would make it difficult for cells to pass through the holes of a filter, and thus be expected to improve the capture rate. However, as shown in Table 7-1, when the amount of blood per hole was 108 nl, the capture rate was not stable and reduced particularly on the lower pressure side of the φ 8 filter and the φ 9.8×6.5 filter. It is considered that since the filtration time was too long, the cells passed through the filters due to their viscoelasticity.

Next, data obtained by varying the filtration pressure with respect to 108 nl of a blood sample to be processed per hole (the total volume of the blood sample to be processed: 8 ml) and 14 nl of a blood sample to be processed per hole (the total volume of the blood sample to be processed: 1 ml) will be shown in the following. As shown in Table 7-2, even under a high flow rate and high pressure, the cells can be captured by reducing the volume of the blood sample to be processed per hole. The fluid transfer conditions may be appropriately determined in accordance with the volume of the blood sample to be processed per hole. In other words, when the fluid transfer conditions are appropriately set so that the flow rate per hole is 30 nl/min or less or the pressure difference is 3.7 kPa or less (or $\Delta P_2$ is 100 Pa or less) in accordance with 14 nl to 108 nl of the blood sample to be processed per hole, a high capture rate of cells can be achieved. For example, when the volume of the blood sample to be processed per hole is 14 nl, 1 ml of blood can be filtered for about 1 minute with a pressure difference of 1.3 kPa in the entire system (i.e., the flow rate per hole is 14 nl/min to 17 nl/min). Thus, high capture rates of both small cancer cells and deformable cancer cells can be achieved. By appropriately setting the volume of the blood sample to be processed per hole, the rare cells can be recovered from a larger volume of the blood sample in a shorter time compared to the conventional method (in which 1 ml of a blood sample is processed for about 5 minutes, and 8 ml of a blood sample is processed for about 40 minutes). Since blood deteriorates over time, the faster it can be processed, the better. Thus, fresh rare cells can be acquired and have a favorable effect on analysis.

Figure 6:
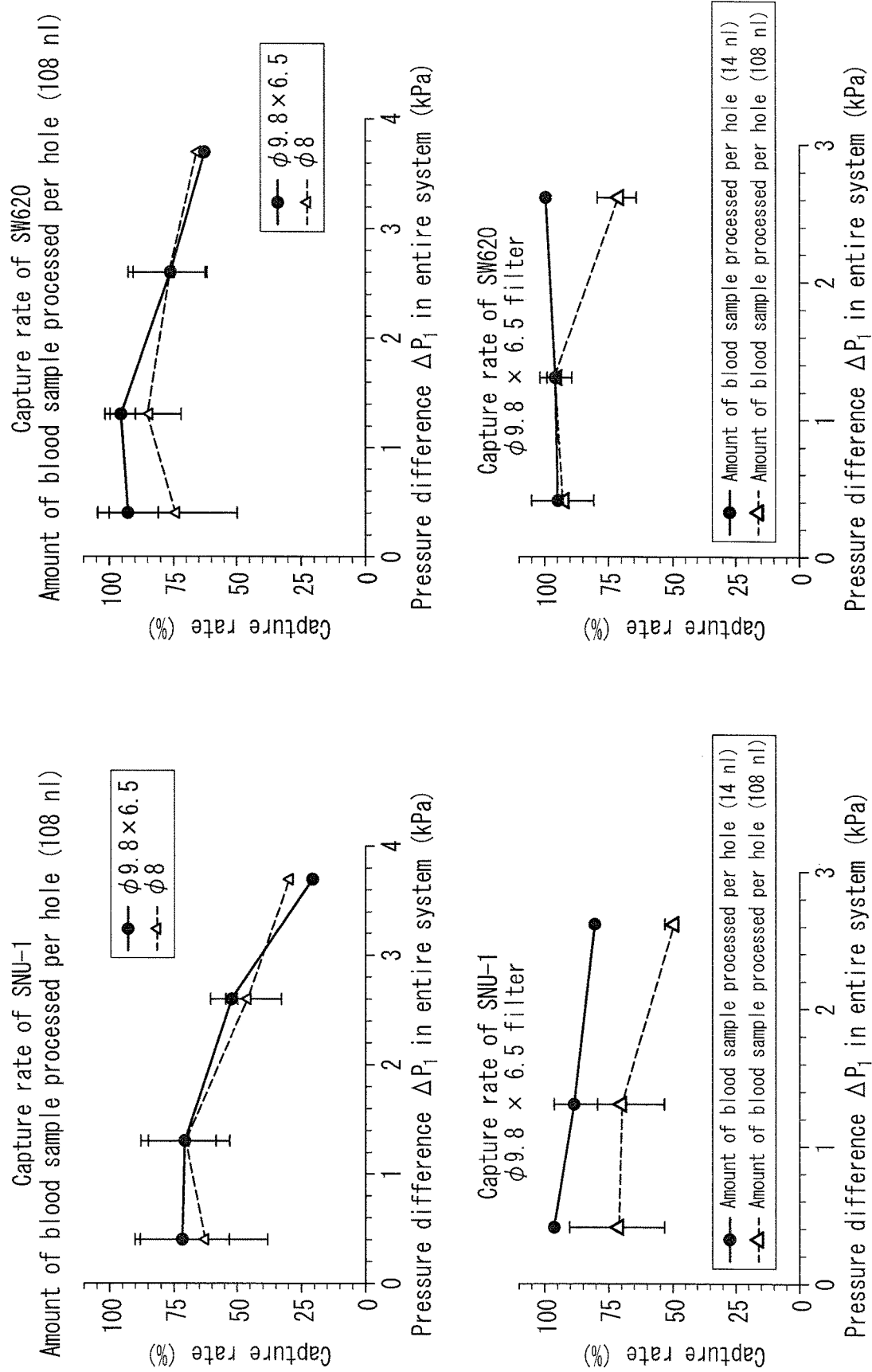
FIG. 6 shows the influence on the capture rate of cells due to a difference in the fluid transfer conditions.

Table 7 and FIG. 6 show the relationship between constant pressure of the fluid transfer conditions, the flow rate, and the recovery rate.

so that the pressure difference in the entire system is 3.7 kPa or less, or the pressure difference between the upper surface and the lower surface of the filter is 100 Pa or less, or the flow rate per hole is 30 nl/min or less in accordance with the amount of blood per hole, i.e., 14 nl to 108 nl of blood per hole, a high capture rate can be achieved.

TABLE 7-1

Capture conditions for 108 nl per hole

| | PBS (−) flow rate μl/sec | | Blood sample | | | | |
|---|---|---|---|---|---|---|---|
| Pressure difference in entire system $\Delta P_1$ (kPa) | Total hole number average flow rate μl/min | Average flow rate per hole nl/min | Total hole number average flow rate μl/min | Average flow rate per hole nl/min | Average flow velocity per hole μm/min | Filtration time of 8 ml blood | Pressure difference between upper surface and lower surface of filter $\Delta P_2$(true circle ϕ8 μm) $\Delta P_2 = Q * 8\eta \, L/(\pi d^4 * N_0)$ |
| within 3.7 ± 0.1 | 7500 | 102 | 1600~2000 | 22~27 | 440~540 | 4~5 min | $\Delta P_2 =$ 80~100 Pa |
| within 2.6 ± 0.1 | 6000 | 81 | 1100~1300 | 15~18 | 300~360 | 6~7 min | $\Delta P_2 =$ 50~70 Pa |
| within 1.3 ± 0.1 | 3000 | 41 | 300~500 | 4~7 | 80~120 | 15~25 min | $\Delta P_2 =$ 16~30 Pa |
| within 0.4 ± 0.1 | 1000 | 14 | 88~130 | 1~2 | 20~40 | 60~90 min | $\Delta P_2 =$ 4~7 Pa |

Capture rate of ϕ8 and ϕ9.8 × 6.5 (108 nl per hole)

| Pressure difference in entire system $\Delta P_1$ (kPa) | Average flow rate per hole nl/min | Capture rate | | | | SD | | | |
|---|---|---|---|---|---|---|---|---|---|
| | | SW620 | | SNU1 | | SW620 | | SNU1 | |
| | | ϕ8 | ϕ9.8 × 6.5 | ϕ8 | ϕ9.8 × 6.5 | ϕ8 | ϕ9.8 × 6.5 | ϕ8 | ϕ9.8 × 6.5 |
| within 3.7 ± 0.1 | 22~27 | 66% | 63% | 30% | 21% | | | | |
| within 2.6 ± 0.1 | 15~18 | 77% | 77% | 47% | 52% | 5% | 15% | 14% | 3% |
| within 1.3 ± 0.1 | 4~7 | 86% | 96% | 72% | 71% | 6% | 6% | 13% | 17% |
| within 0.4 ± 0.1 | 1~2 | 75% | 93% | 63% | 72% | 12% | 12% | 25% | 19% |

※Q: total hole number average flow rate,
a: radius,
L flow path length,
η: blood viscosity,
$N_0$: hold number (all are expressed in SI unit)

TABLE 7-2

Comparison of 14 nl and 108 nl per ϕ9.8 × 6.5 hole

| Pressure difference in entire system (inlet − outlet) $\Delta P_1$(kPa) | Capture rate | | | |
|---|---|---|---|---|
| | SW620 | | SNU1 | |
| | ϕ9.8 × 6.5 (14 nl) | ϕ9.8 × 6.5 (108 nl) | ϕ9.8 × 6.5 (14 nl) | ϕ9.8 × 6.5 (108 nl) |
| within 2.6 ± 0.1 | 100% | 72% | 80% | 50% |
| within 1.3 ± 0.1 | 96% | 96% | 88% | 71% |
| within 0.4 ± 0.1 | 95% | 93% | 96% | 72% |

Figure 7:
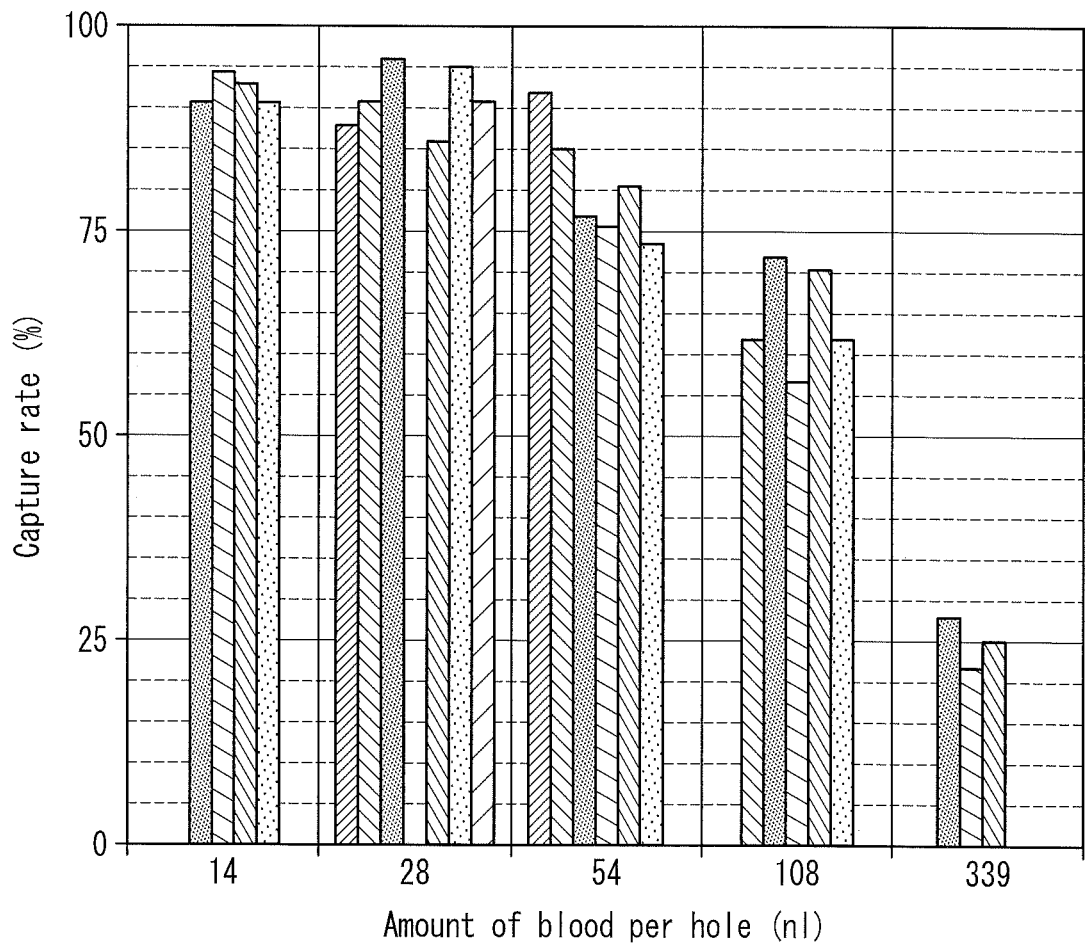
FIG. 7 shows the amount of blood per hole and the capture rate of deformable cells for different types, hole densities, and materials of filters.
Figure 7:
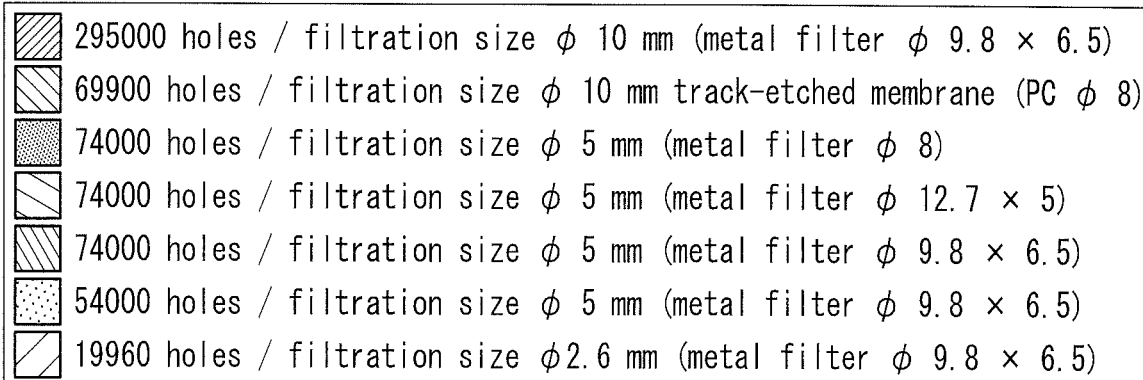

Tables 7-1 and 7-2 confirm that, under the fluid transfer conditions of the present disclosure, when the flow rate is set Using filters that differ in the filtration area, the number of holes, and the hole density, under the filtration conditions shown in Table 8-1, when the volume of the blood sample to be processed per hole was 14 nl to 108 nl, the capture rate of the SNU-1 cells was compared among the filters. Table 8-2 shows the comparative data. The comparative data are also plotted in FIG. 7. The results of the comparison confirm that when the volume of the sample is set in accordance with the number of the holes, or when the amount of blood per hole is set, deformable cells can be captured regardless of the material, the number of the holes, and the density of the filter. Moreover, an appropriate number of the holes can be set with respect to the intended amount of the sample to be processed, and the filtration area can also be reduced.

TABLE 8-1

| Filter | | | | | | | Filtration conditions | | |
|---|---|---|---|---|---|---|---|---|---|
| | | | Pitch | | | | | | |
| Shape | Major axis diameter/Minor axis diameter | Hole area μm² | between centers of holes μm | Hole density hole/mm² | Thickness μm | Opening ratio per area (%) | Material | Filtration area mm² | Total hole number |
| Ellipse | 9.8 × 6.5 | 50 | 19 × 14 | 3759 | 5 | 19 | nickel (metal) | 79 | 295262 |
| Circle | 8 | 50 | Random | 890 | 8 | 4 | PC (resin) | 79 | 69900 |
| Circle | 8 | 50 | 19 × 14 | 3759 | 5 | 19 | nickel | 20 | 73816 |

TABLE 8-1-continued

| | | | | | | | | | |
|---|---|---|---|---|---|---|---|---|---|
| Ellipse | 12.7 × 5 | 50 | 19 × 14 | 3759 | 5 | 19 | nickel (metal) | 20 | 73816 |
| Ellipse | 9.8 × 6.5 | 50 | 19 × 14 | 3759 | 5 | 19 | nickel (metal) | 20 | 73816 |
| Ellipse | 9.8 × 6.5 | 50 | 19 × 19 | 2770 | 5 | 14 | nickel (metal) | 20 | 54390 |
| Ellipse | 9.8 × 6.5 | 50 | 19 × 14 | 3759 | 5 | 19 | nickel (metal) | 5 | 19960 |

| | Filtration conditions | |
|---|---|---|
| Blood flow rate per hole in blood transfer | Pressure difference $\Delta P_1$ in entire system (inlet − outlet) during blood filtration kPa | Pressure difference $\Delta P_1$ in entire system (inlet − outlet) during washing filtration kPa |
| 1~3 nl/min | 1.3 kPa ± 0.1 | 0.4 kPa ± 0.1 |
| 4~7 nl/min | 1.3 kPa ± 0.1 | 0.4 kPa ± 0.1 |
| 4~7 nl/min | 1.3 kPa ± 0.1 | 0.4 kPa ± 0.1 |
| 4~7 nl/min | 1.3 kPa ± 0.1 | 0.4 kPa ± 0.1 |
| 4~7 nl/min | 1.3 kPa ± 0.1 | 0.4 kPa ± 0.1 |
| 4~7 nl/min | 0.7 kPa ± 0.1 | 0.4 kPa ± 0.1 |
| 5 nl/min syringe pump fluid transfer | Flow rate in entire system 100 μl/min syringe pump fluid transfer | Flow rate in entire system 200 μl/min syringe pump fluid transfer |

TABLE 8-2

| Amount of blood per hole (nl) | 295,262 holes/filtration size φ10 mm (metal filter φ9.8 × 6.5) | 69,900 holes/filtration size φ10 mm track-etched membrane (PC φ8) | 73,816 holes/filtration size φ5 mm (metal filter φ8) | 73,816 holes/filtration size φ5 mm (metal filter φ9.8 × 6.5) | 73,816 holes/filtration size φ5 mm (metal filter φ12.7 × 5) | 54,390 holes/filtration size φ5 mm (metal filter φ9.8 × 6.5) | 19,960 holes/filtration size φ2.6 mm (metal filter φ9.8 × 6.5) |
|---|---|---|---|---|---|---|---|
| 14 | — | — | 91% | 93% | 95% | 91% | — |
| 28 | 88% | 91% | 96% | 86% | — | 95% | 91% |
| 54 | 92% | 85% | 77% | 81% | 76% | 74% | — |
| 108 | — | 62% | 72% | 71% | 57% | 62% | — |
| 339 | — | — | 28% | 25% | 22% | — | — |

Figure 8:
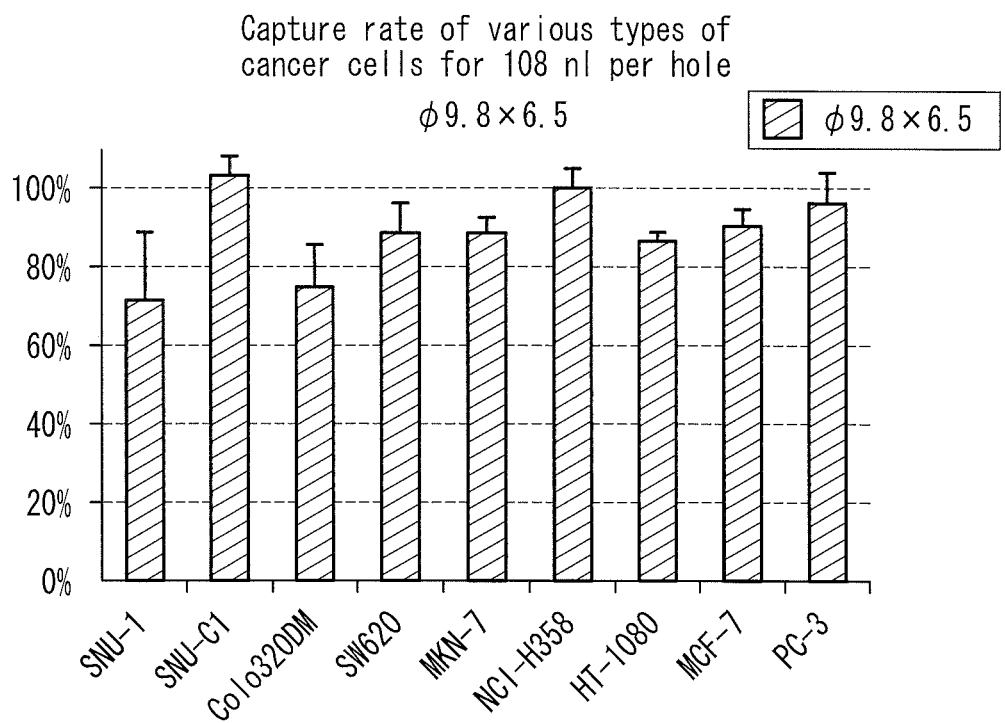
FIG. 8 shows the capture rate of various cancer cells for 108 nl per hole.

Table 9 and FIG. 8 show an example of the results of the relationship between the types of cancer cells and the capture rate when the volume of the blood sample to be processed per hole was 108 nl. A high capture rate was achieved even if the volume of the blood sample to be processed per hole was 108 nl or less.

TABLE 9

Capture rate of cells for 108 nl of blood sample per hole

| | Suspended cell | Suspended, partially adhered | Adherent cell | | | | |
|---|---|---|---|---|---|---|---|
| | | | Gastric | Lung | | Breast | Prostate |
| | Gastric cancer | Colon cancer | cancer | cancer | Sarcoma | cancer | cancer |
| Size at peak position in size distribution (μm) | 17 | 19 | 14 | 13 | 19 | 18 | 17 | 19 | 21 |
| Type of cell | SNU-1 | SNU-C1 | Colo320DM | SW620 | MKN-7 | NCI-H358 | HT-1080 | MCF-7 | PC-3 |
| φ9.8 × 6.5 | 71% | 103% | 75% | 89% | 89% | 101% | 86% | 90% | 97% |
| SD | 17% | 6% | 11% | 8% | 4% | 5% | 3% | 5% | 8% |

Table 9 and FIG. 8 confirm that the method of the present disclosure can efficiently recover various types of cancer cells.

The present disclosure is useful in the field of recovery, measurement, and analysis of rare cells in blood, e.g., in the academic field of medicine and pharmacy and/or in the medical field of treatment, diagnosis, or the like.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

The embodiments have been described, hereinabove. It will be apparent to those skilled in the art that the above methods and apparatuses may incorporate changes and modifications without departing from the general scope of the present disclosure. It is intended to include all such modifications and alterations insofar as they come within the scope of the appended claims or the equivalents thereof. Although the description above contains much specificity, this should not be construed as limiting the scope of the disclosure, but as merely providing illustrations of some of the embodiments of the present disclosure. Various other embodiments and ramifications are possible within its scope.

Furthermore, notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

What is claimed is:

1. A method configured to improve the capture rate of deformable cells while maintaining the capture rate of rare cells in a blood sample using a filter comprising holes with a hole density of 200 holes/mm$^2$ to 40000 holes/mm$^2$, wherein the holes are in the form of an ellipse with a minor axis diameter of 3.0 μm to 15 μm and a major axis diameter of 1.1 times to 3 times as long as the minor axis diameter, or the holes have a shape that contains the ellipse and is in contact with the ellipse on at least two points including both ends of an axis of the ellipse that is the major axis, the method comprising:
separating or detecting rare cells by filtering the blood sample so that a filter capacity per hole of the filter is 6 μl/hole or less expressed in terms of blood, where total blood sample volume (nl) to be processed is from total hole number×10 (nl/hole) to total hole number× 170 (nl/hole) or from total hole area (μm$^2$)×0.2 nl/μm$^2$ to total hole area (μm$^2$)×3.4 nl/μm$^2$ expressed in terms of blood, wherein a pressure difference between an upper surface and a lower surface of the filter during filtration of the blood sample is 4 Pa to 70 Pa, or a flow rate of the blood sample during filtration is 0.25 nl/min per hole to 18 nl/min per hole.

2. The method according to claim 1, wherein the blood sample is filtered in a volume of 1 μl/hole or less expressed in terms of blood with respect to a hole of the filter.

3. The method according to claim 1, wherein the blood sample is filtered in a volume of 0.2 μl/hole or less expressed in terms of blood with respect to a hole of the filter.

4. The method according to claim 1, wherein the filter has a hole density of 300 holes/mm$^2$ to 7000 holes/mm$^2$.

5. The method according to claim 1, wherein the filter has a hole density of 300 holes/mm$^2$ to 5000 holes/mm$^2$.

6. The method according to claim 1, wherein the filter has a hole density of 500 holes/mm$^2$ to 4000 holes/mm$^2$.

7. The method according to claim 1, wherein the filter has a hole density of 800 holes/mm$^2$ to 4000 holes/mm$^2$.

8. The method according to claim 1, wherein the holes are in the form of an ellipse with a minor axis diameter of 4.0 μm to 10 μm and a major axis diameter of 1.1 times to 3 times as long as the minor axis diameter, or the holes have a shape that is in contact with the ellipse on at least two points including both ends of the major axis of the ellipse.

9. The method according to claim 1, wherein an area of a hole in the filter is 15 μm$^2$ to 250 μm$^2$.

10. The method according to claim 1, wherein the area of a hole in the filter is 20 μm$^2$ to 100 μm$^2$.

11. The method according to claim 1, wherein the area of a hole in the filter is 25 μm$^2$ to 80 μm$^2$.

12. The method according to claim 1, wherein the holes are in the form of an ellipse with a minor axis diameter of 5.0 μm to 8 μm and a major axis diameter of 1.1 times to 3 times as long as the minor axis diameter, or the holes have a shape that is in contact with the ellipse on at least two points including both ends of the major axis of the ellipse.

13. The method according to claim 1, comprising:
separating or detecting rare cells by processing the blood sample in an amount indicated by "Total volume of blood sample to be processed (nl)" using a filter in which a number of the holes is defined by "Hole number (holes)=Total volume of blood sample to be processed (nl)/170 to Total volume of blood sample to be processed (nl)/10" or a total area of the holes is defined by "Total hole area (μ$^2$)=Total volume of blood sample to be processed (nl/3.4 (nl/μm$^2$) to Total volume of blood sample to be processed (nl)/0.2 (nl/μm$^2$)".

14. The method according to claim 1, comprising:
separating or detecting rare cells by filtering the blood sample so that the filter capacity per hole of the filter is 10 nl/hole to 108 nl/hole expressed in terms of blood.

15. The method according to claim 1, wherein the blood sample is filtered in a volume of 0.1 μl/hole or less expressed in terms of blood with respect to a hole of the filter.

16. The method according to claim 1, wherein the blood sample is filtered in a volume of 0.06 μl/hole or less expressed in terms of blood with respect to a hole of the filter.

17. The method according to claim 1, wherein a number of the holes in the filter is more than 10000 holes.

18. The method according to claim 1, wherein the filter is made of at least one selected from the group consisting of glass, plastic, metal, and a combination thereof.

19. The method according to claim 1, wherein the rare cells are selected from the group consisting of cancer cells, circulating tumor cells, vascular endothelial cells, vascular endothelial precursor cells, cancer stem cells, epithelial cells, hematopoietic stem cells, mesenchymal stem cells, embryonal cells, and a combination thereof.

20. A method for analyzing rare cells in a blood sample comprising:
separating or detecting rare cells by the method according to claim 1, and then analyzing the rare cells by a method including kinetic observation or activity measurement of the rare cells.

* * * * *